US007962205B2

(12) United States Patent
Okura et al.

(10) Patent No.: US 7,962,205 B2
(45) Date of Patent: Jun. 14, 2011

(54) HUMAN SUBJECT INDEX ESTIMATION APPARATUS AND METHOD

(75) Inventors: Masashi Okura, Saitama (JP); Yasuhiro Kasahara, Tokyo (JP)

(73) Assignee: Tanita Corporation, Tokyo (JP)

(*) Notice: Subject to any disclaimer, the term of this patent is extended or adjusted under 35 U.S.C. 154(b) by 798 days.

(21) Appl. No.: 11/926,945

(22) Filed: Oct. 29, 2007

(65) Prior Publication Data

US 2008/0146961 A1 Jun. 19, 2008

(30) Foreign Application Priority Data

Dec. 13, 2006 (JP) ................................ 2006-336162

(51) Int. Cl.
A61B 5/00 (2006.01)
A61B 5/05 (2006.01)
A61B 5/103 (2006.01)
A61B 5/117 (2006.01)
C30B 33/06 (2006.01)
C30B 15/00 (2006.01)
G01B 5/08 (2006.01)

(52) U.S. Cl. ............ 600/547; 600/301; 600/587; 117/1; 117/25.11; 702/157

(58) Field of Classification Search .................. 600/301, 600/547, 587; 177/1, 25.11; 702/157
See application file for complete search history.

(56) References Cited

U.S. PATENT DOCUMENTS

| 4,557,271 | A | * | 12/1985 | Stoller et al. ................... 600/547 |
| 4,895,163 | A | * | 1/1990 | Libke et al. ..................... 600/547 |
| 4,947,862 | A | * | 8/1990 | Kelly ............................ 600/547 |
| 5,579,782 | A | * | 12/1996 | Masuo .......................... 600/547 |
| 5,720,296 | A | * | 2/1998 | Cha ............................... 600/554 |
| D424,191 | S | * | 5/2000 | Sarrazin ....................... D24/107 |
| D436,323 | S | * | 1/2001 | Lubs .............................. D10/87 |
| D436,545 | S | * | 1/2001 | Lubs .............................. D10/87 |
| 6,256,532 | B1 | * | 7/2001 | Cha ............................... 600/547 |
| 6,292,690 | B1 | * | 9/2001 | Petrucelli et al. ............. 600/547 |
| 6,360,124 | B1 | * | 3/2002 | Iwabuchi ...................... 600/547 |
| 6,369,337 | B1 | * | 4/2002 | Machiyama et al. ....... 177/25.13 |
| 6,472,617 | B1 | * | 10/2002 | Montagnino ................. 177/126 |
| 6,473,643 | B2 | * | 10/2002 | Chai et al. .................... 600/547 |
| 6,487,445 | B1 | * | 11/2002 | Serita et al. .................. 600/547 |

(Continued)

FOREIGN PATENT DOCUMENTS

JP 11-113870 4/1999

(Continued)

OTHER PUBLICATIONS

European Search Report dated Jan. 21, 2008 relating to EP 07018103.

Primary Examiner — Max Hindenburg
Assistant Examiner — Sean P Dougherty
(74) Attorney, Agent, or Firm — Hogan Lovells US LLP

(57) ABSTRACT

A CPU (170) of a human subject index estimation apparatus (1) computes a waist circumference based on body weight measured by a weight scale (110) and bioelectric impedance measured by a bioelectric impedance measurement unit (200A), and information such as age and height which was input through input unit (150). The computed waist circumference is stored, along with the information such as age and height, in a third storage unit (140) that is a rewritable non-volatile memory. The CPU (170) displays the waist circumference on display unit (160).

16 Claims, 18 Drawing Sheets

U.S. PATENT DOCUMENTS

| | | | |
|---|---|---|---|
| RE37,954 E * | 1/2003 | Sato et al. | 600/547 |
| 6,516,221 B1 * | 2/2003 | Hirouchi et al. | 600/547 |
| 6,519,491 B2 * | 2/2003 | Ishikawa et al. | 600/547 |
| 6,538,215 B2 * | 3/2003 | Montagnino et al. | 177/25.16 |
| 6,567,692 B1 * | 5/2003 | Kohashi et al. | 600/547 |
| 6,621,013 B2 * | 9/2003 | Tanida et al. | 177/4 |
| 6,643,542 B1 * | 11/2003 | Kawanishi | 600/547 |
| 6,752,760 B2 * | 6/2004 | Kouou | 600/301 |
| 6,766,272 B2 * | 7/2004 | Serita | 702/156 |
| 6,782,340 B1 * | 8/2004 | Komatsu et al. | 702/173 |
| 6,850,797 B2 * | 2/2005 | Kawanishi et al. | 600/547 |
| 6,865,415 B2 * | 3/2005 | Kawanishi | 600/547 |
| 6,905,464 B2 * | 6/2005 | Kawanishi et al. | 600/301 |
| 6,920,352 B2 * | 7/2005 | Shimomura et al. | 600/547 |
| 6,963,035 B2 * | 11/2005 | Honda et al. | 177/25.19 |
| 7,060,914 B2 * | 6/2006 | Suzuki | 177/238 |
| 7,130,680 B2 * | 10/2006 | Kodama et al. | 600/547 |
| 7,146,207 B2 * | 12/2006 | Masuda et al. | 600/547 |
| 7,252,635 B2 * | 8/2007 | Itagaki | 600/300 |
| 7,262,703 B2 * | 8/2007 | Collins | 340/573.1 |
| 7,336,992 B2 * | 2/2008 | Shiokawa | 600/547 |
| 7,340,295 B2 * | 3/2008 | Shiokawa | 600/547 |
| 7,483,735 B2 * | 1/2009 | Liu et al. | 600/547 |
| 7,634,312 B2 * | 12/2009 | Kawanishi | 600/547 |
| 7,764,991 B2 * | 7/2010 | Yamazaki et al. | 600/547 |
| 2001/0011043 A1 * | 8/2001 | Ishikawa et al. | 473/316 |
| 2002/0052697 A1 * | 5/2002 | Serita | 702/30 |
| 2002/0123695 A1 * | 9/2002 | Kawanishi | 600/547 |
| 2003/0097081 A1 * | 5/2003 | Masuda et al. | 600/587 |
| 2005/0124865 A1 * | 6/2005 | Kawanishi | 600/300 |
| 2006/0025706 A1 | 2/2006 | Chen | 600/587 |

FOREIGN PATENT DOCUMENTS

| | | |
|---|---|---|
| JP | 2002355222 A * | 12/2002 |
| WO | 0234132 A1 | 2/2002 |

* cited by examiner

FIG. 4A  MEASUREMENT IS STARTED

FIG. 4B  USE ▲▼ KEY TO INPUT YOUR HEIGHT

FIG. 4C  USE ▲▼ KEY TO INPUT YOUR AGE

FIG. 4D  MALE FEMALE

FIG. 4E
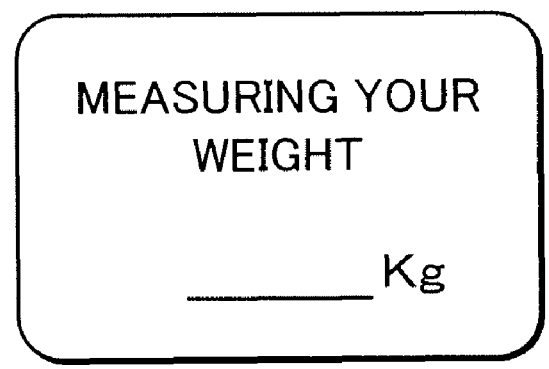
FIG. 4F
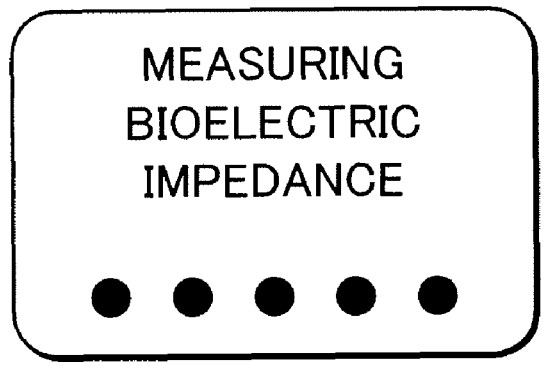
FIG. 4G
| WEIGHT | 82.3kg |
|---|---|
| BODY FAT PERCENTAGE | 23.5% |
| VISCERAL FAT CROSS-SECTIONAL AREA | 135cm$^2$ |
| WAIST | 82.5cm |
| HIP | 95.3cm |
| WAIST:HIP RATIO | 0.86 |
FIG. 4H
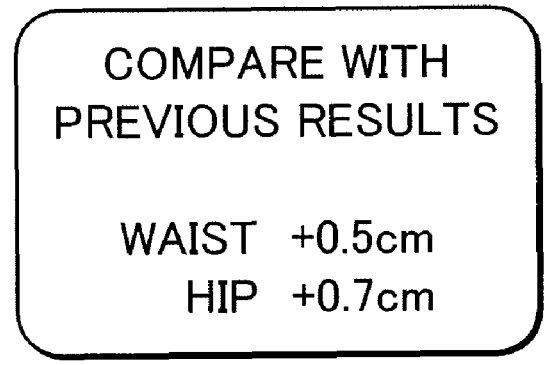

$I_{ref}$

WHOLE BODY

RIGHT LEG

LEFT LEG

RIGHT ARM

LEFT ARM

HUMAN SUBJECT INDEX ESTIMATION APPARATUS AND METHOD

BACKGROUND OF THE INVENTION

1. Field of the Invention

The present invention relates to an apparatus for estimating the circumference of a predetermined level between the abdomen and the buttocks levels, such as the waist level and the hip level, of a human subject, and relates to a method therefor.

2. Description of Related Art

Metabolic syndrome has recently been discussed as a new concept of disease; it is suggested that a combination of adult diseases such as obesity, high blood pressure, hyperlipemia, and diabetes are often not independent from one another, but have a common cause in visceral adiposity, specifically fat deposits primarily around the visceral organs.

Waist circumference is now widely used as an index that clearly indicates the amount of visceral fat. Criteria for metabolic syndrome have recently been drawn up in Japan by The Examination Committee of Criteria for Metabolic Syndrome, including as its members, the Japan Atherosclerosis Society, Japan Diabetes Society, Japanese Society of Hypertension, Japan Society for the Study of Obesity, The Japanese Circulation Society, The Japanese Society of Nephrology, The Japanese Society on Thrombosis and Hemostasis, and The Japanese Society of Internal Medicine. The criteria require, as one condition for metabolic syndrome, an increased waist circumference that is equal to or greater than 85 cm for men and equal to or greater than 90 cm for women. From 2008, waist circumference will be an essential component of medical examinations for adults in Japan.

It is to be noted that, in the present invention, "circumference" is the length of the circumference at a predetermined position of the human body. For example, the waist circumference is the length of the circumference of the abdomen at the waist level, and the hip circumference is the length of the circumference at the hips at the level of the buttocks.

Additionally, the awareness of health matters has increased among people, regardless of gender. Women, in particular, coupled with their desire for thinness, have strong desires for external attractiveness, such as a smaller waist and hip size, as well as for improvements in the internal body in terms of body fat percentage and metabolism.

Tape measures are generally used for measuring waist circumferences. In addition, Japanese Patent Application Laid-Open Publication JP-11-113870-A discloses a band-type measurement apparatus provided with an electrically readable scale.

In a case in which tape measures or band-type measures are used to measure waist circumference, however, there is a problem in that the results of measurements vary depending on the degree of tightening of the tape measure or belt. Also, wrapping a tape measure or a belt parallel to the floor all the way around is not always possible. Furthermore, errors in measurement are associated with various definitions of the waist; that is, there is no commonly agreed upon definition of the waist among those who perform the measurements.

SUMMARY OF INVENTION

The present invention was made in consideration of the above, and the present invention has as objects to provide a human subject index estimation apparatus that enables an indirect measurement of a circumference at a predetermined position between the levels of the abdomen and the hips without the need to wrap a tape measure or a belt around the abdomen or the hips of a human body, and to provide a method therefor.

To achieve the above objects, a human subject index estimation apparatus according to the present invention estimates the circumference of a human subject at a predetermined position between the levels of the waist and the hips, and the apparatus is provided with a weight scale that measures the weight (body weight) of the human subject, and a computer (for example, a CPU 170 shown in FIG. 1) that executes a computation in accordance with an equation (A), thereby estimating the circumference, the equation (A) having the form $Y=a1*W+f(k) \ldots (A)$, in which Y is the circumference, W is the weight, a1 is a constant, k is a variable, and f(k) is a function of plural variables, the variables including the weight and at least one of sex, race, age, height, body mass index, bioelectric impedance, body fat percentage, and body fat mass.

The circumference at a predetermined position between the abdomen and the level of the buttocks of a human body is large for those with heavy builds and is small for those with thin builds. That is, the correlation is high between body weight and the circumference of the predetermined position. In the present invention, since the circumference is estimated by performing a predetermined computation based on the weight, the circumference at the predetermined position can be estimated without the need to actually measure the circumference. Performing an actual measurement using a tape measure and the like as in a conventional method is subject to error due to the degree of tightening of the tape measure or the measuring position. However, the circumference is automatically estimated in the present invention, thereby enabling a simple and precise measurement of the circumference. The equation (A) may preferably be derived from a multiple regression analysis based on actually measured circumferences and measured body weights.

Furthermore, since the computation is performed using, as variables, in addition to the body weight, at least one of sex, race, age, height, body mass index, bioelectric impedance, body fat percentage, and body fat mass of a human subject, the accuracy of the estimation of the circumference is improved. The body fat percentage and the body fat mass may be those which are estimated based on bioelectric impedance or those which have been input through operation of an input unit by an operator of the apparatus.

Additionally, the present invention provides a human subject index estimating method for estimating the circumference of a human subject at a predetermined position between the levels of the waist and the hips, and the method includes steps of measuring the body weight of the human subject and executing a computation in accordance with the equation (A). According to the present invention, the circumference of a predetermined position can be determined without using a tape measure because the circumference is predicted by executing a predetermined computation based on the body weight and at least one of the other indices.

Preferably, in the human subject index estimation apparatus or in the human subject index estimating method the constant a1 and a constant contained in the function f(k) are changed depending on at least one of the sex and race of the human subject. Because men and women have different physiques, the circumference at a predetermined position usually differs between men and women having the same body weight. Also, the physiques of Asians and Europeans differ. According to the present invention, constants used in the computation are changed depending on at least one of sex and race, and circumference can thereby be more precisely estimated. Since the form of the equation (A) used in the computation is the same for men and women, simply changing a constant enables the computation of the circumference. Furthermore, by using constants stored in advance depending on sex, the computation program can be used for both sexes.

In a preferred embodiment of the present invention, in a case in which the predetermined position is at the level of the waist, the computation of the equation (A) is executed using, as the function f(k), a function f(Z,H,E) as shown in an equation (B) which takes the form $f(Z,H,E)=a2*Z/H+a3*E \ldots$ (B), where Z is bioelectric impedance, H is height, E is age, and a2 and a3 are constants. In this case, since age is used as a variable, the differences in physique depending on age can be reflected in the estimated circumference. Furthermore, since the height that has been normalized using bioelectric impedance is used as a variable, the accuracy of prediction is improved in estimating waist circumference. In particular, in a case in which a foot-to-foot bioelectric impedance is measured, the accuracy is considerably increased. It should be noted that in the present invention the "waist" is at the level of the navel.

In yet another preferred embodiment of the present invention, in a case in which the predetermined position is at the level of the hips, the computation of the equation (A) is executed using, as the function f(k), the function f(% Fat, BMI) as shown in equation (C) which takes the form $f(\% Fat, BMI)=a4*\% Fat*BMI \ldots$ (C), where % Fat is body fat percentage, BMI is body mass index, and a4 is a constant. In this case, since the body fat percentage and body mass index are used as variables, the circumference at the hips can be more accurately estimated. It should be noted that the "hips" is the part at which the buttocks has the greatest circumference.

Furthermore, the above human subject index estimation apparatus has a bioelectric impedance measurement device that measures bioelectric impedance between the left foot and the right foot, and the computer executes the computation of the equation (A) using the measured bioelectric impedance. Also, the human subject index estimating method further has a step of measuring bioelectric impedance between the left foot and the right foot, and the computation of the equation (A) is executed using the measured bioelectric impedance. In this case, electrodes used for measuring bioelectric impedance are provided at a base of the weight scale so that bioelectric impedance can be measured in a position in which a human subject stands on the weight scale for weighing.

Furthermore, the human subject index estimation apparatus may be provided with a bioelectric impedance measurement device that has first to fourth electrodes contacting the left foot, the right foot, the left hand, and the right hand, respectively; fifth to eighth electrodes contacting the left foot, the right foot, the left hand, and the right hand, respectively; an electric current supplier that supplies an electric current between two of the first to fourth electrodes; and a potential difference detector that detects a potential difference between two of the fifth to eighth electrodes, and the bioelectric impedance measurement device may switch the two electrodes to which the electric current is supplied and the two electrodes between which a potential difference is detected, to measure the bioelectric impedance of plural portions of the human subject, and the bioelectric impedance measurement device computes a bioelectric impedance of a trunk of the human subject based on the measured bioelectric impedance of the plural portions, and the computer executes the computation of the equation (A) using the measured bioelectric impedance. Also, the human subject index estimating method further has the steps of supplying an electric current between two of the first to fourth electrodes contacting the left foot, the right foot, the left hand, and the right hand, respectively; detecting a potential difference between two of the fifth to eighth electrodes contacting the left foot, the right foot, the left hand, and the right hand, respectively, switching the two electrodes to which the electric current is supplied and the two electrodes between which a potential difference is detected, to measure the bioelectric impedance of plural portions of the human subject, and computing a bioelectric impedance of a trunk of the human subject based on the measured bioelectric impedance of the plural portions, and executing the computation of the equation (A) using the measured bioelectric impedance. In this case, bioelectric impedance of plural portions of a human body is used to derive bioelectric impedance of the trunk of the human body. Since the bioelectric impedance of the trunk is more strongly related to the circumference of the human body between the abdomen and the buttocks levels than the bioelectric impedances of other portions of the body, the accuracy in estimating the circumference of the predetermined position is improved.

Additionally, the human subject index estimation apparatus may be provided with a storage device that stores a circumference actually measured at the predetermined location as an initial circumference value and stores the variable measured in a measurement of a first time as an initial variable value, and the computer may, in a measurement at a second time and subsequent times, i) compute a variable difference value that is a difference between the variable measured this time and the initial variable value read from the storage device, ii) execute the computation of the equation (A) using the variable difference value instead of using the variable, thereby computing one of an increased value and a decreased value of the circumference, and iii) compute the circumference as estimated at this time by adding the increased or decreased value of the circumference to the initial circumference value read from the storage. Also, the human subject index estimating method may further have the steps of storing in a storage device a circumference actually measured at the predetermined location as an initial circumference value and storing the variable measured in a measurement of a first time as an initial variable value, and the computing step may include, in a measurement at a second time and subsequent times, i) computing a variable difference value that is a difference between the variable measured this time and the initial variable value read from the storage device, ii) executing the computation of the equation (A) using the variable difference value instead of using the variable, thereby computing one of an increased value and a decreased value of the circumference, and iii) computing the circumference as estimated at this time by adding the increased or decreased value of the circumference to the initial circumference value read from the storage. In this case, since an actually measured value of circumference is used as a standard value and one of an estimated increased value and a decreased value is added to the standard value, the accuracy in the prediction of the circumference is considerably improved.

BRIEF DESCRIPTION OF THE DRAWINGS

With reference to the accompanying drawings, various embodiments of the present invention will be described hereinafter. In the drawings:

FIGS. 4A to 4H are diagrams showing examples of screens on a display unit;

DETAILED DESCRIPTION OF PREFERRED EMBODIMENTS

1. First Embodiment

1-1. Configuration of a Human Subject Index Estimation Apparatus

Figure 1:
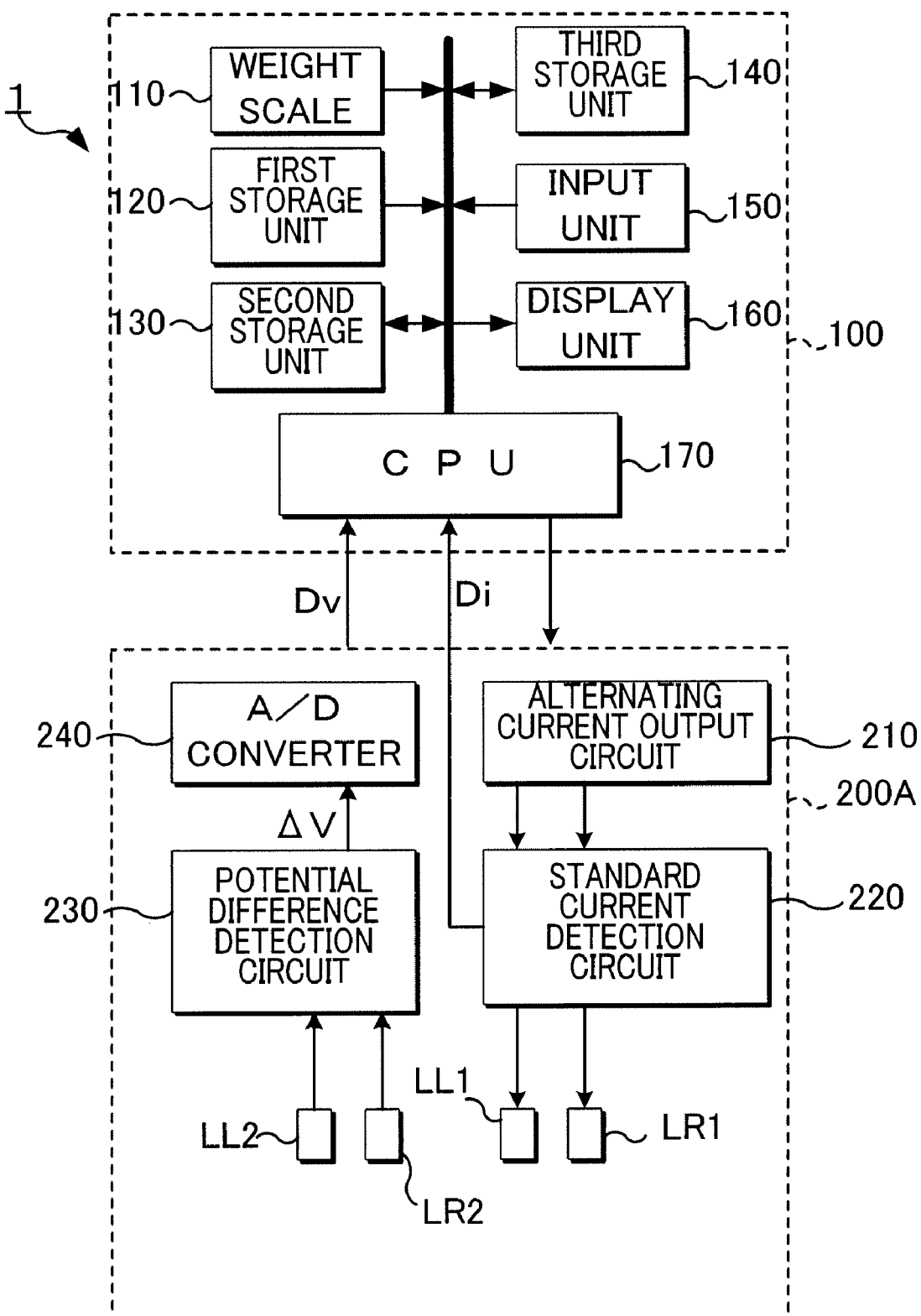
FIG. 1 is a block diagram showing a configuration of a human subject index estimation apparatus according to a first embodiment of the present invention.

FIG. 1 is a block diagram showing a configuration of a human subject index estimation apparatus 1 according to an embodiment of the present invention. The human subject index estimation apparatus 1 has a control unit 100 that measures weight and controls operation of the apparatus 1 and a bioelectric impedance measurement unit 200A that measures bioelectric impedance between the bottoms of both feet of a human subject. The management unit 100 has a weight scale 110, a first storage unit 120, a second storage unit 130, and a third storage unit 140, and an input unit 150, and a display unit 160. These units are connected to a CPU (Central Processing Unit) 170 via a bus. CPU 170 functions as a central control that controls the entire apparatus. CPU 170 operates by receiving clock signals supplied from a clock signal generation circuit (not shown). When a power switch (not shown) is turned on, power is supplied from a power supply circuit to each unit.

Weight scale 110 measures a body weight of a human subject to output weight data via the bus to CPU 170. First storage unit 120 is a non-volatile memory and is, for example, a ROM (Read Only Memory). There is stored in the first storage unit 120 a control program for controlling the entire apparatus. CPU 170 executes a predetermined computation that will be described later in accordance with the control program, thereby estimating a waist circumference of a human subject to generate waist circumference data.

Second storage unit 130 is a volatile memory and is, for example, DRAM (Dynamic Random Access Memory). Second storage unit 130 functions as a work area for CPU 170 and stores data when CPU 170 performs a predetermined computation. Third storage unit 140 is a rewritable non-volatile memory and is, for example, a flash memory or an EEPROM (Electrically Erasable and Programmable Read Only Memory). Third storage unit 140 is for storing basic data that indicates characteristics of a body of a human subject such as height, age, and sex, as well as past weight data and waist circumference data estimated in the past.

Figure 2:
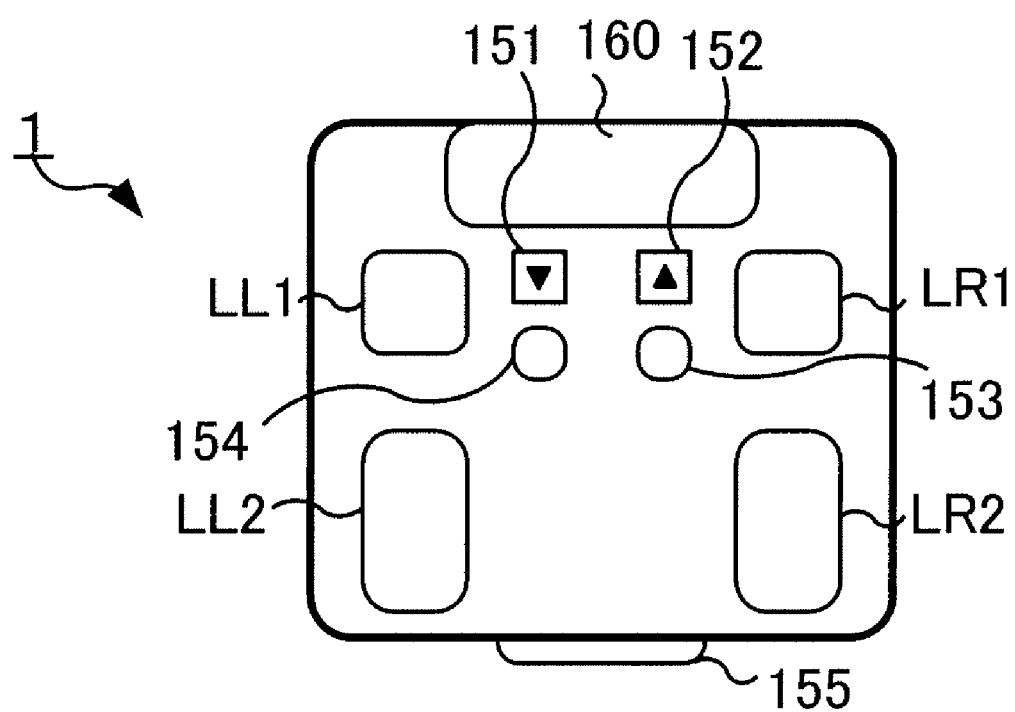
FIG. 2 is a plane view of the apparatus.

Input unit 150 has various switches, and when an operator operates the switches, information such as height, age, and sex is input. Display unit 160 has a function of displaying results of measurement or estimation such as weight and waist circumference and messages prompting an operator of the apparatus 1 to input various types of indices relating the human subject. Specifically, as shown in FIG. 2, display unit 160 is positioned in the central upper portion of the body of the apparatus. Input unit 150 has switches 151 to 155. Specifically, switches 151 and 152 function as an up switch and a down switch, respectively, for inputting numerical values and selecting an item from a menu; switches 153 and 154 function to confirm the input details; and switch 155 functions as a power switch.

Bioelectric impedance measurement unit 200A measures a bioelectric impedance of a human subject by a so-called "four-electrode method". Bioelectric impedance measurement unit 200A has an alternating current output circuit 210, a standard current detecting circuit 220, a potential difference detecting circuit 230, an A/D converter 240, and electrodes LL1, LL2, LR1, and LR2. As shown in FIG. 2, electrode LL1 is located to face the toes of the left foot; electrode LL2 is located to face the heel of the left foot; electrode LR1 is located to face the toes of the right foot; and electrode LR2 is located to face the heel of the right foot.

Alternating current output circuit 210 generates, as a standard current $I_{ref}$, an alternating current with a frequency and an effective value defined in the control program. Standard current detecting circuit 220 detects an amount of the standard current $I_{ref}$ to output the detected amount as current data Di for supply to CPU 170, so that the standard current $I_{ref}$ is sent into a human subject (a human body). Potential difference detecting circuit 230 detects a potential difference between electrode LL2 and electrode LR2 to generate a potential difference signal $\Delta V$. A/D converter 240 converts the potential difference signal $\Delta V$ from an analog to digital signal for output as voltage data Dv to CPU 170. CPU 170 computes bioelectric impedance based on the voltage data Dv and current data Di (=Dv/Di).

1-2. Operation of Human Subject Index Estimation Apparatus

Figure 3:
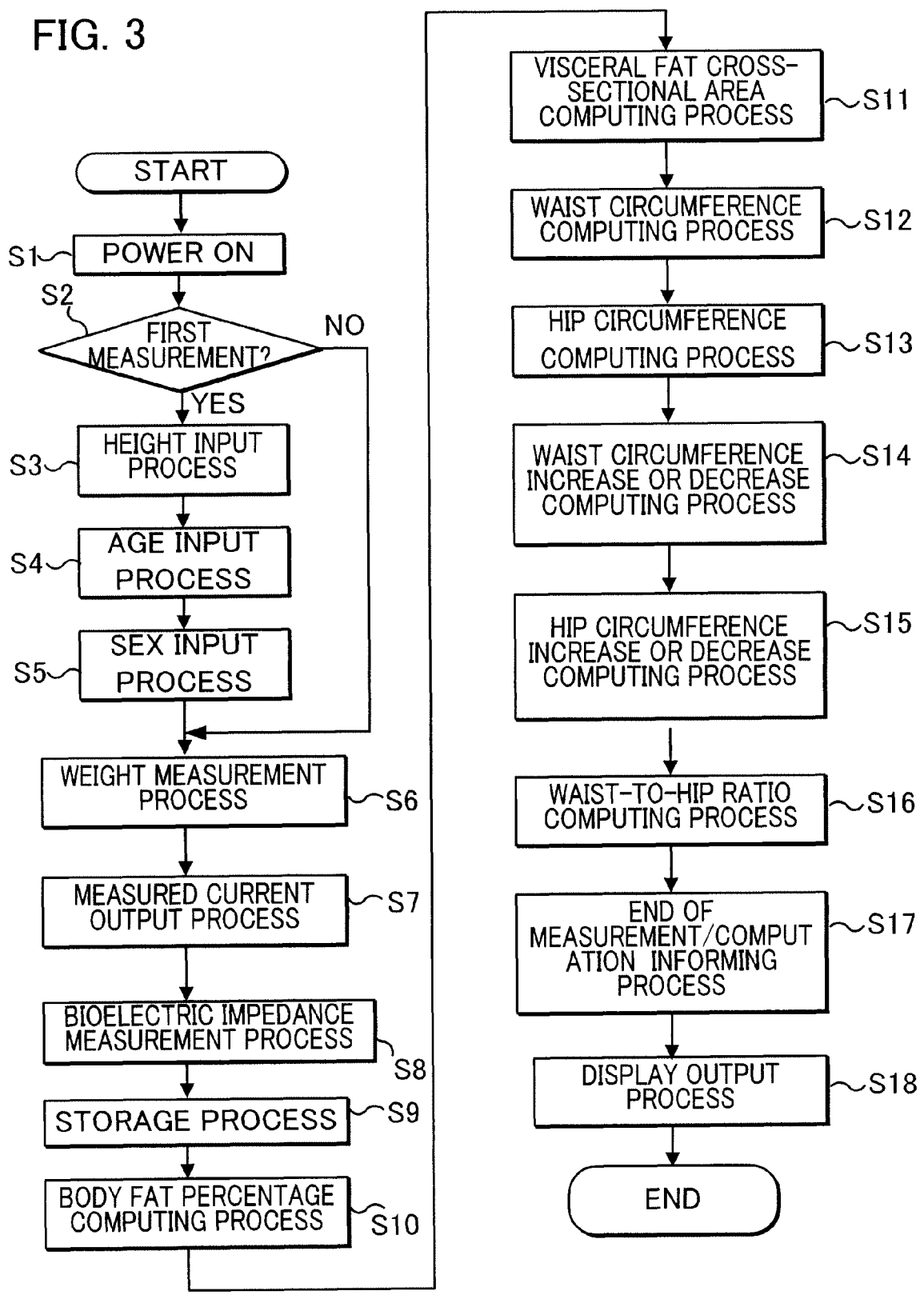
FIG. 3 is a flowchart showing operation of the apparatus.

Description will be next given of an operation of human subject index estimation apparatus 1. FIG. 3 is a flow chart for describing an operation of human subject index estimation apparatus 1. FIGS. 4A to 4H show examples of screens displayed on display unit 160.

As shown in FIG. 3, when an operator operates switch 155 to turn the power on (Step S1), CPU 170 displays a screen shown in FIG. 4A on display unit 160, thereby informing the operator of the start of the operation (Step S2). CPU 170 subsequently determines whether this is the first time a measurement is taken (Step S2). Specifically, CPU 170 accesses a third storage unit 140 to find out whether basic data such as height has previously been stored. In a case in which the basic data is stored, then it is not a first-time measurement; therefore, the determination of Step S2 is negative, whereas in a case in which the basic data is not stored, it is a first-time measurement; and the determination of Step S2 in turn changes to the affirmative.

When the determination of Step S2 is affirmative, CPU 170 proceeds to Step S3 to execute a height input process. CPU 170, in the height input process, displays the screen shown in FIG. 4B on display unit 160, thereby prompting the operator to input the height of the human subject. When the operator then operates switch 153 to fix the input height, CPU 170 writes in third storage unit 140 height data indicating the height of the human subject. CPU 170 then performs an age input process (Step S4). Specifically, CPU 170 displays the screen shown in FIG. 4C on display unit 160, thereby prompting the operator to input the age of the human subject. When the operator operates switches 151 to 153 to input the age, CPU 170 writes in third storage unit 140 age data indicating the age of the human subject. CPU 170 next performs a sex input process (Step S5). CPU 170 in the sex input process displays the screen shown in FIG. 4D on display unit 160, thereby prompting the operator to input the sex of the human subject. When the operator operates switch 154, the sex displayed on the screen is switched between male and female. The operator then fixes the input sex by operating switch 153, CPU 170 writes in third storage unit 140 sex data indicating the sex of the human subject. The basic data is thus input in human subject index estimation apparatus 1 through the processes of Steps S3 to S5. It should be noted in this example that it is assumed that the operator is the human subject himself or herself. However, the operator need not necessarily be the human subject, and the operator may be another person who assists in the measurement of the human subject indices using human subject index estimation apparatus 1.

Subsequently, CPU 170 proceeds to Step S6 to perform a weighing process in which the screen shown in FIG. 4E is displayed on display unit 160. When the operator mounts human subject index estimation apparatus 1, weight data measured by weight scale 110 is supplied through the bus to CPU 170. CPU 170 displays the weight of the operator, and in the meantime, CPU 170 writes the weight data in third storage unit 140.

CPU 170 subsequently executes a standard current output process (Step S7). In this process, CPU 170 controls alternating current output circuit 210 to have the circuit output the standard current $I_{ref}$. Bioelectric impedance is used to estimate body fat percentage. The body fat percentage can be computed by estimating the percentage of fat in the weight. The composition of a human body is largely divided into muscle tissue, bone tissue, adipose (fat) tissue, and body fluids, and among these, fat is an electrical insulator (i.e., it is a poor conductor of electrical current). The frequency of the standard current $I_{ref}$ is preferably set so that the above composition of the human body is reflected. In this example, the frequency is set to 50 kHz in consideration of the above points of view.

CPU 170 then performs a bioelectric impedance measurement process (Step S8). In this process, CPU 170 computes bioelectric impedance Z based on the current data Di detected in the standard current detecting circuit 220 and the voltage data Dv detected in the potential difference detecting circuit 230. In the present embodiment, the bioelectric impedance Z is measured using the four-electrode method. By using this method, the effect of the contact resistance between electrodes LL1, LL2, LR1, and LR2 is minimized, thereby enabling a precise measurement of the bioelectric impedance Z. In the meantime, CPU 170 displays the screen shown in FIG. 4F on display unit 160 during a period in which the bioelectric impedance is being measured, to thereby inform the operator that the measurement is currently being performed. When the measurement of the bioelectric impedance Z is completed, CPU 170 stores the measured bioelectric impedance Z in third storage unit 140 (Step S9).

Subsequently, CPU 170 performs a body fat percentage computing process (Step S10). Specifically, CPU 170 estimates the body fat percentage % Fat in accordance with the following Equation (1):

$$\% \text{ Fat} = f1 \cdot Z \cdot W/H^2 - f2 \qquad (1)$$

where f1 and f2 are constants.

In the first term of Equation (1), $W/H^2$ is a body mass index (BMI) and indicates a degree of obesity. The constants f1 and f2 are derived through performing a multiple regression analysis based on body fat percentage obtained by a DXA method (Dual-energy X-ray Absorptiometry method). The DXA method, with the use of two types of radiation of different wavelength, determines the composition of a human body from the amounts of transmitted rays, thereby enabling a highly precise measurement of body fat percentage. However, this requires a large apparatus, and the human subject is inevitably exposed to radiation, even though the exposure is extremely small. On the other hand, the bioelectric impedance method used in the present embodiment provides a simple and secure way of estimating body fat percentage % Fat.

Figure 5:
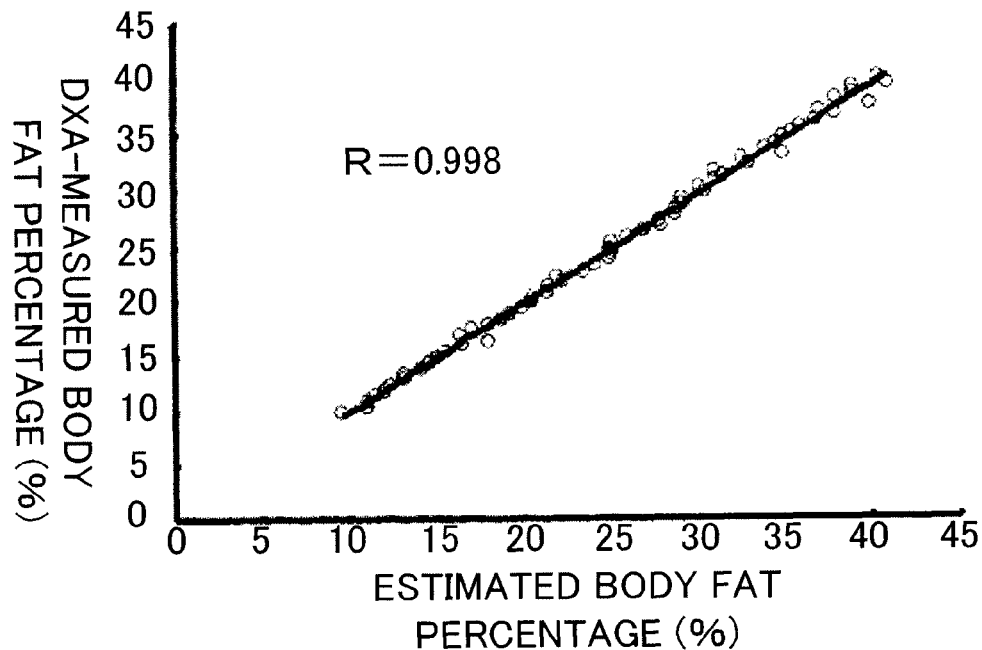
FIG. 5 is a graph showing a relationship between actually measured body fat percentage and estimated body fat percentage.

FIG. 5 shows a correlation between body fat percentage obtained by the DXA method and that obtained by computing Equation (1). As is clear from the figure, a high correlation is obtained if the constants f1 and f2 are properly determined.

Subsequently, CPU 170 performs a visceral fat cross-sectional area computing process (Step S11), to thereby estimate visceral fat cross-sectional area VFA. Specifically, CPU 170 estimates the visceral fat cross-sectional area VFA in accordance with the following Equation (2):

$$VFA = v1 * Z*W/H^2 - v2 + v3*E \qquad (2)$$

where v1, v2, and v3 are constants, and E is age.

The third term, "v3*E", of Equation (2) includes "E" because visceral fat in a human body generally tends to increase since people exercise less as they age. The constants v1 to v3 of Equation (2) are derived by performing a multiple regression analysis based on visceral fat cross-sectional area VFA obtained by the CT method (Computed Tomography method). In the CT method, x-ray beams of narrow bandwidth are directed from multiple directions to a cross section of a human body, and transmitted x-ray beams are detected so that spatial distributions of degrees of x-ray absorption in the cross section may be computed by a computer and an image thereof may be generated. The CT method, like the DXA method, enables highly precise measurement of visceral fat cross-sectional area. However, it requires a large apparatus, and the human subject is inevitably exposed to radiation, even though the amount of exposure is extremely small. On the other hand, the bioelectric impedance method used in the present embodiment provides a simple and secure way of estimating visceral fat cross-sectional area VFA.

Figure 6:
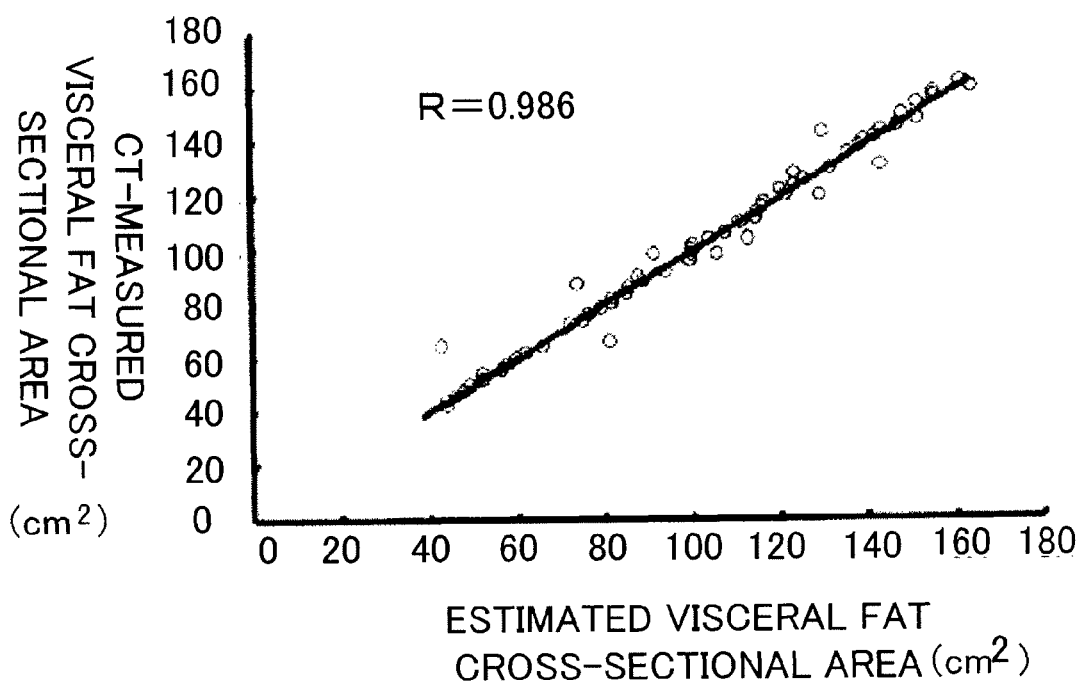
FIG. 6 is a graph showing a relationship between actually measured visceral fat cross-sectional area and estimated visceral fat cross-sectional area.

FIG. 6 shows a correlation between visceral fat cross-sectional area obtained by the CT method and that obtained by computing Equation (2). As is clear from the figure, a high correlation is obtained if the constants v1 to v3 are properly determined.

Subsequently, CPU 170 performs a waist circumference computing process (Step S12) to estimate waist circumference WC. Specifically, CPU 170 estimates the waist circumference WC in accordance with the following Equation (3). It should be noted that, in the present embodiment, waist circumference WC is the circumference of the abdomen at the level of the navel.

$$WC = w1 * Z/H + w2*W + w3*E \qquad (3),$$

where w1, w2, and w3 are constants, W is weight, and E is age.

Figure 7A:
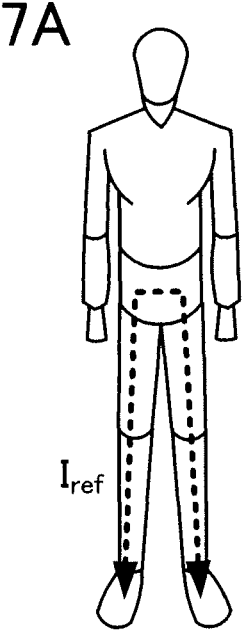
FIGS. 7A and 7B are diagrams for describing the measurement of bioelectric impedance.
Figure 7B:
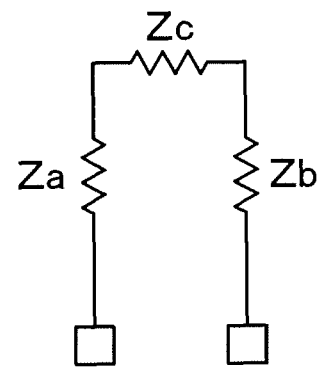

The first term of Equation (3), "w1*Z/H", uses bioelectric impedance Z and height H as parameters. The bioelectric impedance of the present embodiment is measured between both feet, and therefore, the standard current $I_{ref}$ flows as shown in FIG. 7A. As shown in FIG. 7B, with the bioelectric impedance of the left foot being Za, that of the right foot Zb, and that of a portion of the trunk Zc, measured bioelectric impedance is derived from the following Equation (4):

$$Z = Za + Zb + Zc \qquad (4)$$

The bioelectric impedance Zc of the portion of the trunk is the most important parameter in estimating waist circumference WC. Since the legs of a person increase in length the taller a person is, the ratio of Za and Zb in the measured bioelectric impedance Z is larger for a taller person. The measured bioelectric impedance Z is normalized by height H for this reason, so that the effect of differences in height among human subjects is minimized.

The second term "w2*W" has weight W as a parameter because the waist circumference WC increases as the weight W increases. The third term, "w3*E", has a parameter of age E. The physique changes as the age advances even if the weight W remains the same. Such difference in physique depending on age can be corrected by the third term.

Figure 8:
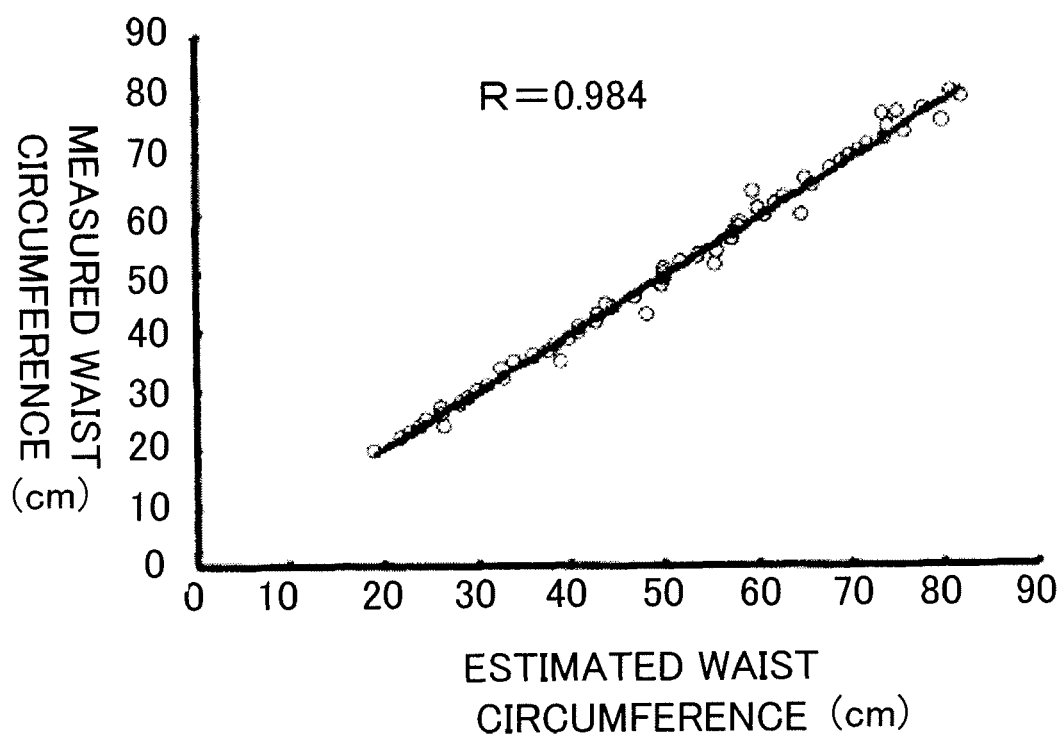
FIG. 8 is a graph showing a relationship between actually measured waist circumference and estimated waist circumference in accordance with Equation (3)

The constants w1 to w3 of Equation (3) are derived by performing a multiple regression analysis based on actually measured waist circumference WC. FIG. 8 shows a correlation between actually measured waist circumference WC and that obtained by computing Equation (3). As is clear from the figure, a high correlation is obtained if the constants w1 to w3 are properly determined.

Subsequently, CPU 170 performs a hip circumference computing process (Step S13) to estimate hip circumference HC. Specifically, CPU 170 estimates the hip circumference HC in accordance with the following Equation (5). It should be noted that, in the present embodiment, hip circumference HC is the circumference at the level of the buttocks at a position at which the buttocks protrude the most.

$$HC = h1 * \% Fat * W/H^2 + h2*W \qquad (5)$$

where h1 and h2 are constants, and the % Fat is estimated body fat percentage.

The first term of Equation (5) has parameters of body fat percentage % Fat and body mass index (BMI=W/H$^2$). The first term is introduced because the buttocks is the portion of a human body that has a particularly high ratio of fat and also because a person with a higher BMI tends to be obese and has a larger hip size.

Figure 9:
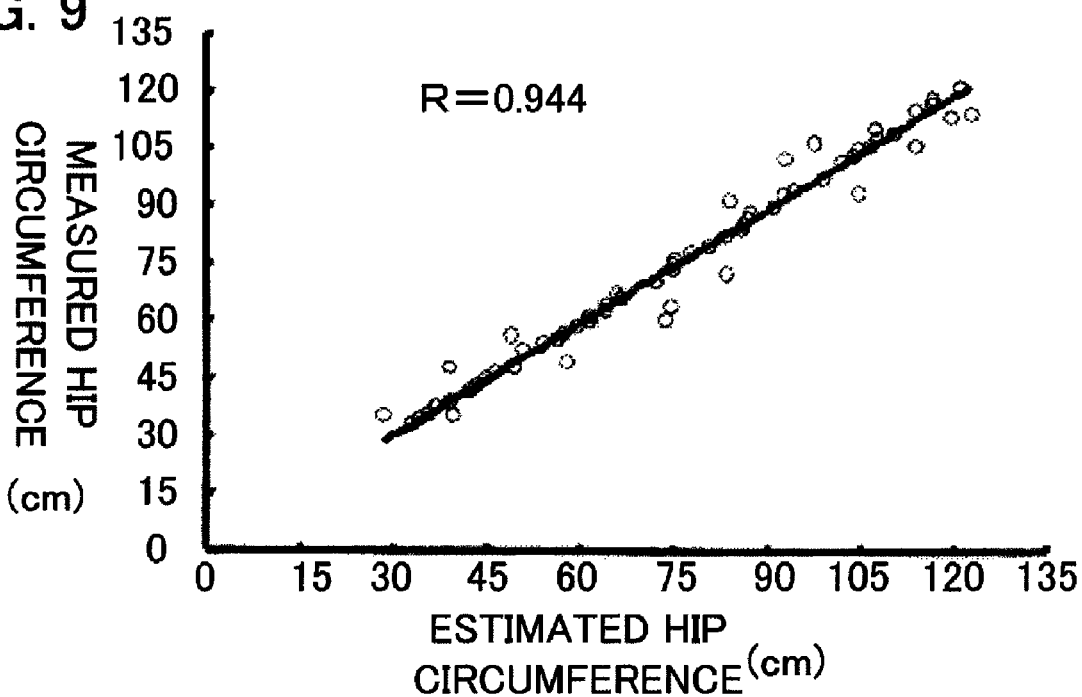
FIG. 9 is a graph showing a relationship between actually measured circumference at the level of the hips and estimated circumference at the level of the hips in accordance with Equation (5)

The second term has a parameter of weight W since a heavier person tends to have a larger hip size. The constants h1 and h2 of Equation (5) are derived by performing a multiple regression analysis based on actually measured hip circumference HC. FIG. 9 shows a correlation between actually measured hip circumference WC and that obtained by computing Equation (5). As is clear from the figure, a high correlation is obtained if the constants h1 and h2 are properly determined.

Subsequently, CPU 170 performs a waist circumference increase or decrease computing process (Step S14). In this process, CPU 170 reads from third storage unit 140 the waist circumference WC estimated in the immediately previous measurement and then computes a difference between the waist circumference estimated at this time and that of the previous measurement, to obtain decrease and increase value ΔWC. CPU 170 subsequently performs a hip circumference increase or decrease computing process (Step S15). In this process, CPU 170 reads from third storage unit 140 the hip circumference HC estimated in the immediately previous measurement and then computes a difference between the hip circumference estimated this time and that of the previous measurement, to obtain decrease and increase value ΔHC. Furthermore, CPU 170 performs a waist-to-hip ratio computing process (Step S16). Specifically, the waist circumference computed in Step S12 is divided by the hip circumference obtained in Step S13, to compute the waist-to-hip ratio. Waist-to-hip ratio WH is an index that indicates a health condition. A person having a larger value of the waist-to-hip ratio WH is considered to not be in good health.

CPU 170 then performs an end-of-measurement and computation informing process (Step S17) to inform the operator that the measurement has ended. CPU 170 subsequently performs a display output process (Step S18) to display a result of the measurement on display unit 160. For example, as shown in FIG. 4G, weight W, body fat percentage % Fat, visceral fat cross-sectional area VFA, estimated waist circumference WC, estimated hip circumference HC, and waist-to-hip ratio WH are displayed on display unit 160. Furthermore, CPU 170 displays, on display unit 160, waist increased or decreased value ΔWC and hip increased or decreased value ΔHC, each indicating the difference between the immediately previous measurement.

As described in the foregoing, according to the present invention, waist circumference WC and hip circumference HC can be indirectly measured without having to directly measure the circumference by using such means as tape measures because waist circumference WC and hip circumference HC are estimated using bioelectric impedance Z. As a result, errors can be avoided that are likely to be caused due to misalignments of measuring devices and the degree of tightening of a tape measure being irregular when measurements are performed manually.

1-3: Modifications of the First Embodiment

Whereas in the above human subject index estimation apparatus 1 the waist circumference WC is estimated in accordance with Equation (3), waist circumference WC may be estimated in accordance with at least one of the following modes.

(1) First Mode

In the waist circumference computing process (Step S12), CPU 170 may estimate waist circumference WC in accordance with Equation (6) as follows:

$$WC=w4+w2*W \qquad (6)$$

where w2 and w4 are constants, and W is weight.

Figure 10:
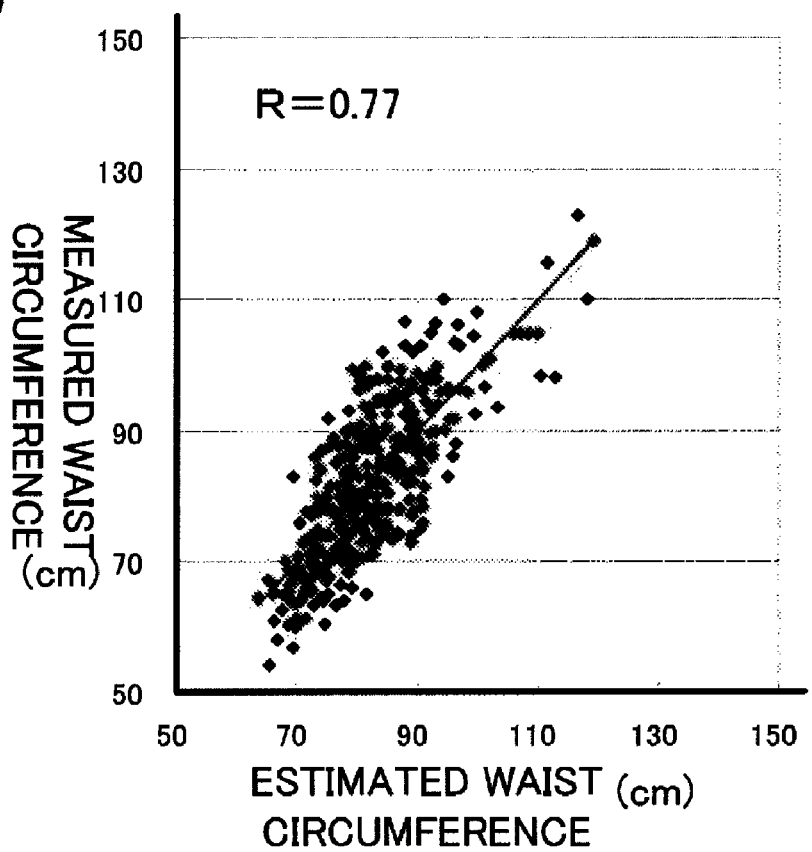
FIG. 10 is a graph showing a relationship between actually s measured waist circumference and estimated waist circumference in accordance with Equation (6)

The constants w2 and w4 are derived by performing a multiple regression analysis based on actually measured waist circumference WC. FIG. 10 shows a correlation between the actually measured waist circumference WC and that obtained by computing Equation (6). As is clear from the figure, a correlation index R of "0.77" is obtained when the constants w2 and w4 are properly selected.

Figure 11:
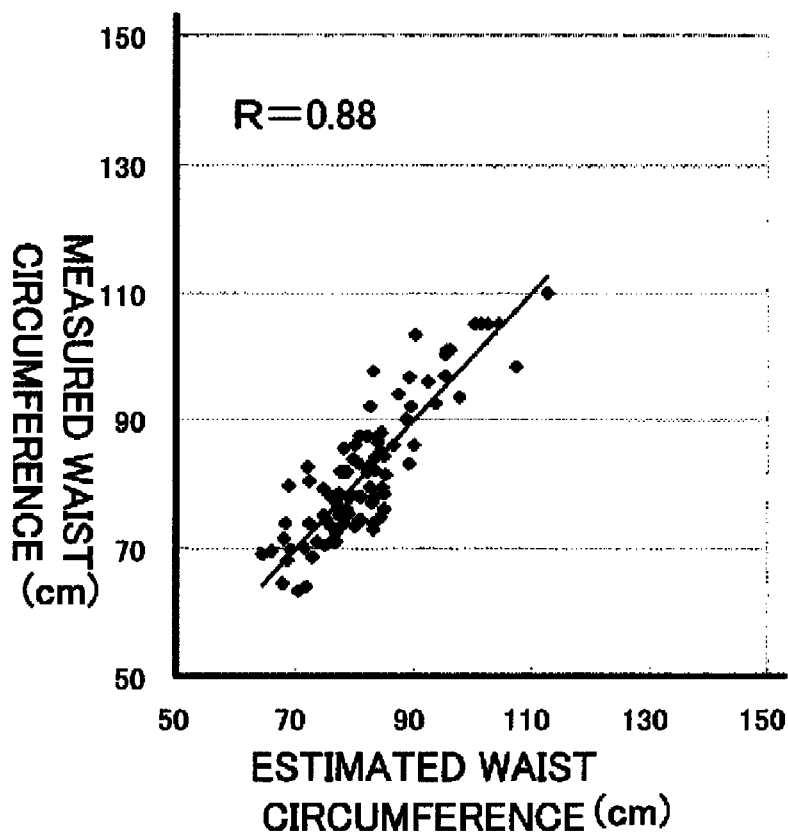
FIG. 11 is a graph showing a relationship between actually measured waist circumference and estimated waist circumference in accordance with Equation (6) in a case in which the human subjects are male.
Figure 12:
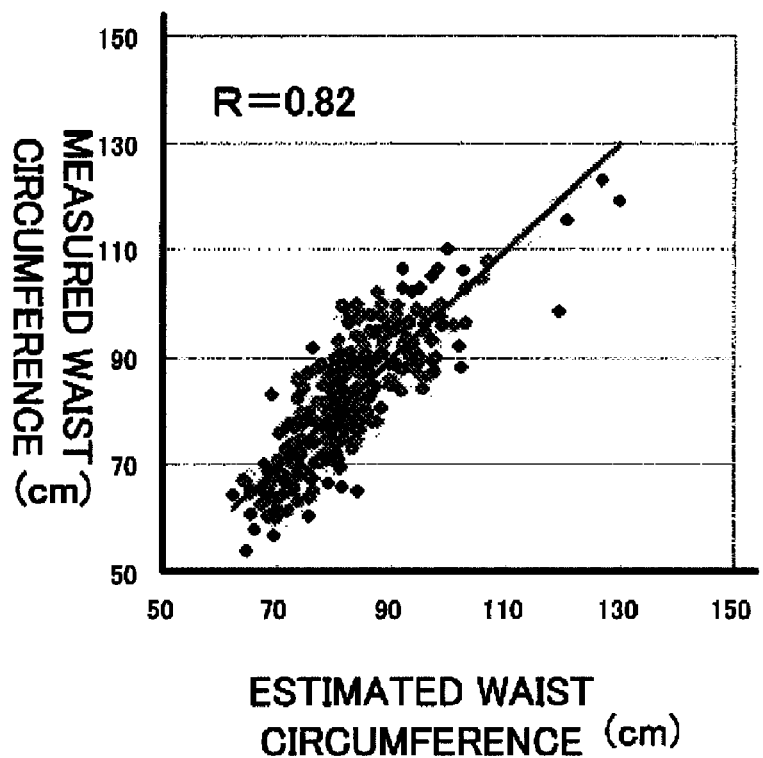
FIG. 12 is a graph showing a relationship between actually measured waist circumference and estimated waist circumference in accordance with Equation (6) in a case in which the human subjects are female.

Furthermore, the constants w2 and w4 of Equation (6) can be changed depending on the sex of a human subject. For example, by selecting proper values of the constants w2 and w4 for male human subjects, a correlation index R of "0.88" is obtained in a case in which all of the human subjects are male as shown in FIG. 11; and by selecting proper values of the constants w2 and w4 for female human subjects, a correlation index R of "0.82" is obtained in a case in which all of the human subjects are female as shown in FIG. 12. Thus, using sex as a parameter for estimating waist circumference WC increases the accuracy of the prediction.

(2) Second Mode

In the waist circumference computing process (Step S12), CPU 170 may estimate the waist circumference WC in accordance with Equation (7) as follows:

$$WC=w4+w2*W+w5*W/H^2 \qquad (7)$$

where w2, w4, and w5 are constants, W is weight, and H is height.

Figure 13:
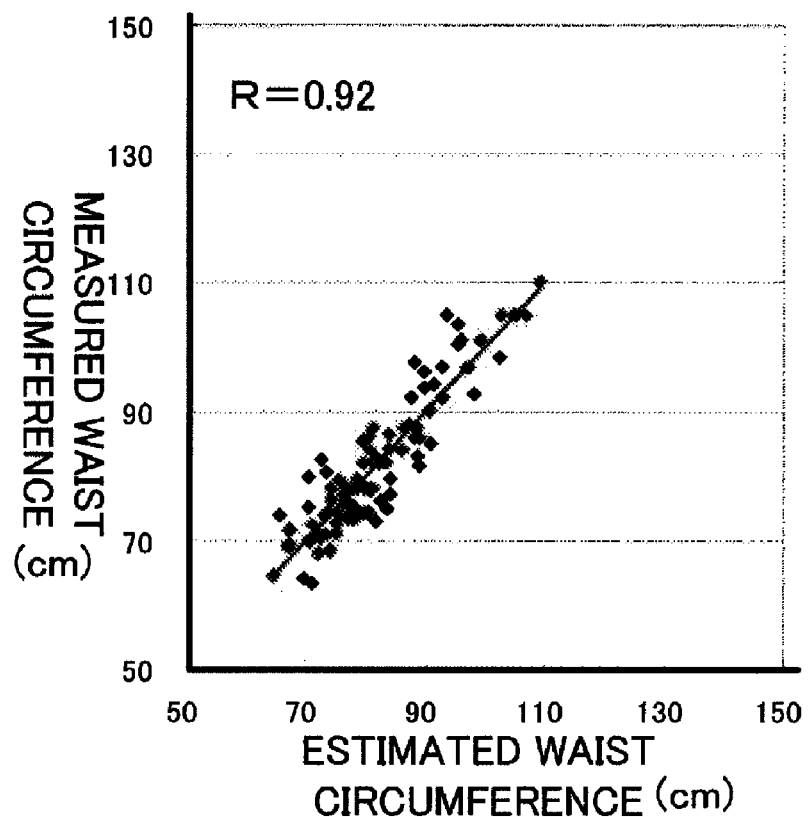
FIG. 13 is a graph showing a relationship between actually measured waist circumference and estimated waist circumference in accordance with Equation (7)

Equation (7) differs from Equation (6) in that Equation (7) has the third term having the BMI(=W/H$^2$) as a variable. Like the above first mode, the constants may be preferably changed depending on sex. By selecting proper values of the constants w2, w4, and w5 for male human subjects, a correlation index R of "0.92" is obtained as shown in FIG. 13. Thus, using BMI as a parameter increases the accuracy in the estimation.

(3) Third Mode

In the waist circumference computing process (Step S12), CPU 170 may estimate waist circumference WC in accordance with Equation (8) as follows:

$$WC=w4+w2*W+w6*H \qquad (8)$$

where w2, w4, and w6 are constants, W is weight, and H is height.

Figure 14:
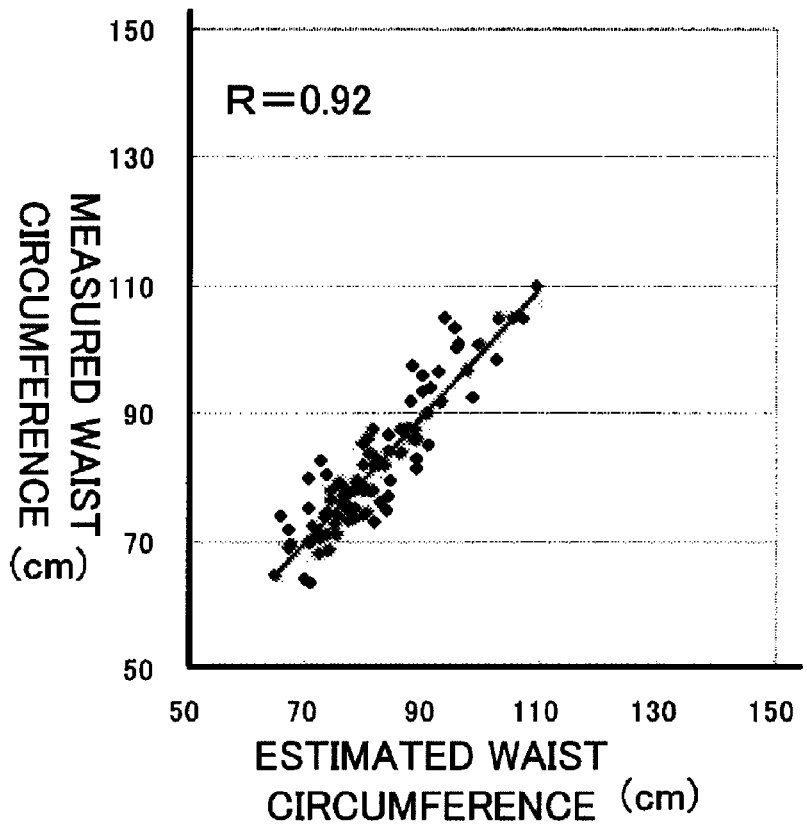
FIG. 14 is a graph showing a relationship between actually measured waist circumference and estimated waist circumference in accordance with Equation (8)

Equation (8) differs from Equation (6) in that Equation (8) has the third term that has the height H as a variable. Like the above first mode, the constants w2, w4, and w6 may be preferably changed depending on sex. By selecting proper values of the constants w2, w4, and w6 for male human subjects, a correlation index R of "0.92" is obtained as shown in FIG. 14. Thus, using height H as a parameter enhances the accuracy in the estimation.

(4) Fourth Mode

In the waist circumference computing process (Step S12), CPU 170 may estimate waist circumference WC in accordance with Equation (9) as follows:

$$WC=w4+w2*W+w7*E \qquad (9)$$

where w2, w4, and w7 are constants, W is weight, and E is age.

Figure 15:
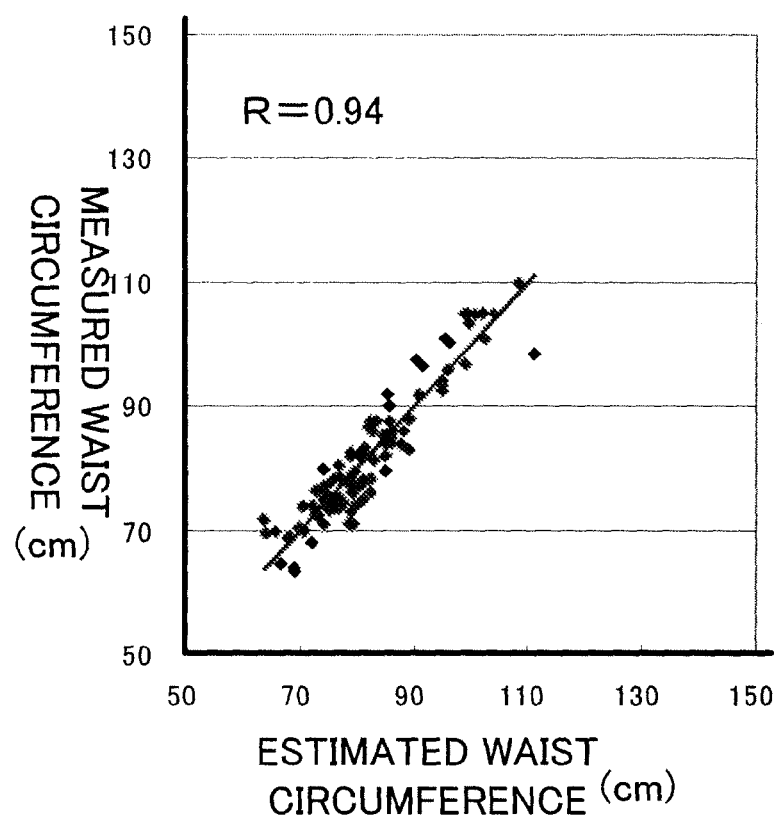
FIG. 15 is a graph showing a relationship between actually measured waist circumference and estimated waist circumference in accordance with Equation (9)

Equation (9) differs from Equation (6) in that Equation (9) has the third term that has age E as a variable. Like the above first mode, the constants w2, w4, and w7 may be preferably changed depending on sex. By selecting proper values of the constants w2, w4, and w7 for male human subjects, a correlation index R of "0.94" is obtained as shown in FIG. 15. Thus, using age E as a parameter increases the accuracy in the estimation.

(5) Fifth Mode

In the waist circumference computing process (Step S12), CPU 170 may estimate waist circumference WC in accordance with Equation (10) as follows:

$$WC=w4+w1*Z/H+w2*W \qquad (10)$$

where w1, w2, and w4 are constants, W is weight, Z is bioelectric impedance, and H is height.

Figure 16:
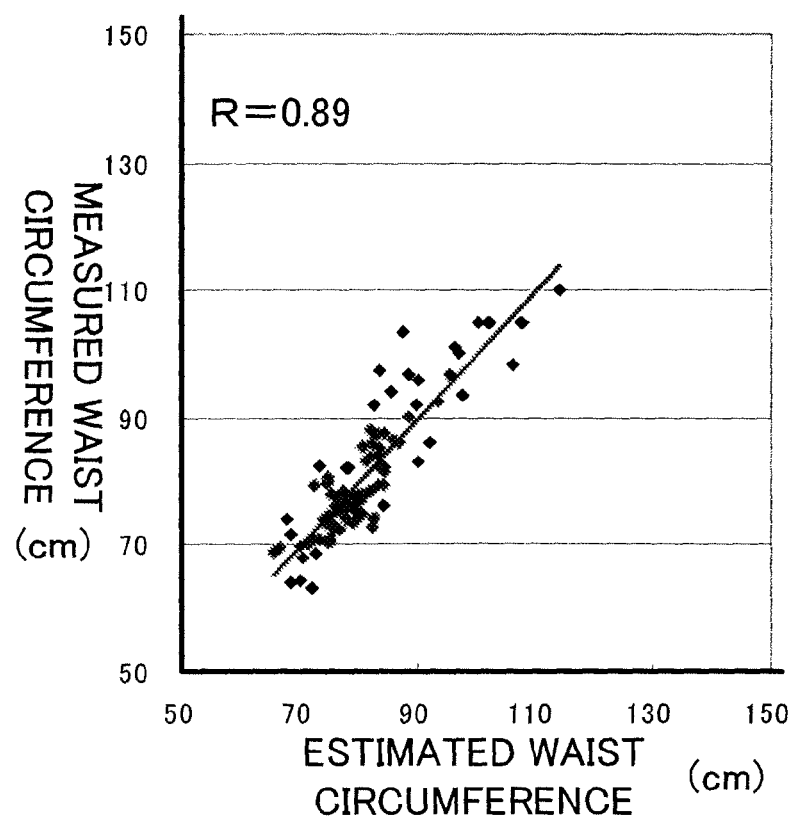
FIG. 16 is a graph showing a relationship between actually measured waist circumference and estimated waist circumference in accordance with Equation (10)

Equation (10) differs from Equation (6) in that Equation (10) has the second term that has a parameter obtained by dividing bioelectric impedance Z by height H. Like the above first mode, the constants w1, w2, and w4 may be preferably changed depending on sex. By selecting proper values of the constants w1, w2, and w4 for male human subjects, a correlation index R of "0.89" is obtained as shown in FIG. 16. Thus, using a parameter obtained by dividing bioelectric impedance Z by height H enhances the accuracy of the estimation.

(6) Sixth Mode

In the waist circumference computing process (Step S12), CPU 170 may estimate waist circumference WC in accordance with Equation (11) as follows:

$$WC=w4+w8*Z/H^2+w2*W \qquad (11)$$

where w2, w4, and w8 are constants, W is weight, Z is bioelectric impedance, and H is height.

Figure 17:
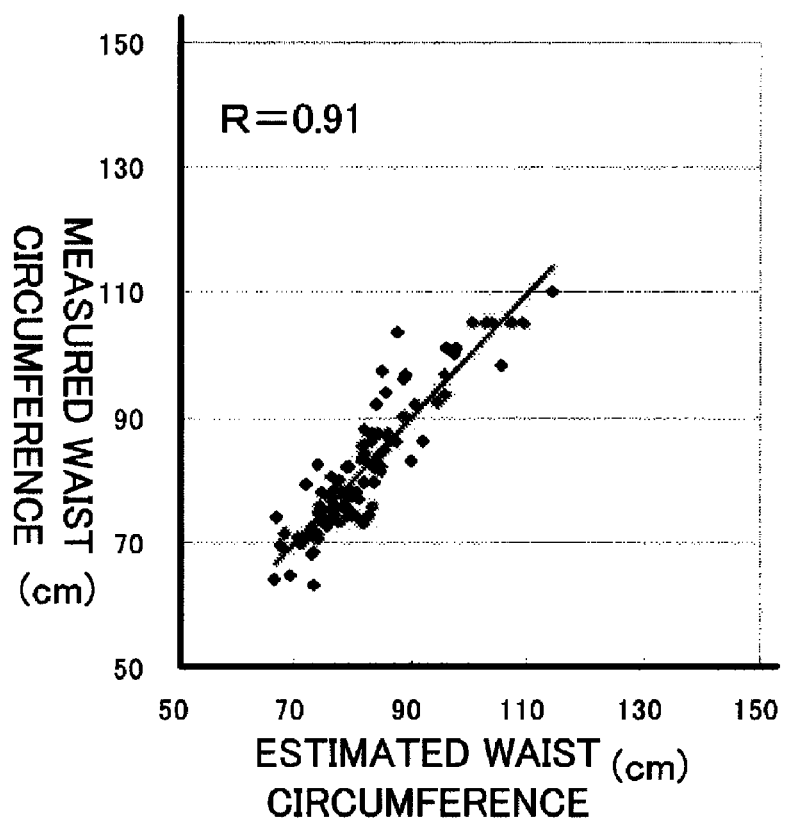
FIG. 17 is a graph showing a relationship between actually measured waist circumference and estimated waist circumference in accordance with Equation (11)

Equation (11) differs from Equation (6) in that Equation (11) has the second term that has a parameter obtained by dividing bioelectric impedance Z by the square of the height H. Like the above first mode, the constants w2, w4, and w8 may be preferably changed depending on sex. By selecting proper values of the constants w2, w4, and w8 for male human subjects, a correlation index R of "0.91" is obtained as shown in FIG. 17. Thus, using a parameter obtained by dividing bioelectric impedance Z by the square of the height H enhances the accuracy in the estimation.

(7) Seventh Mode

Figure 18:
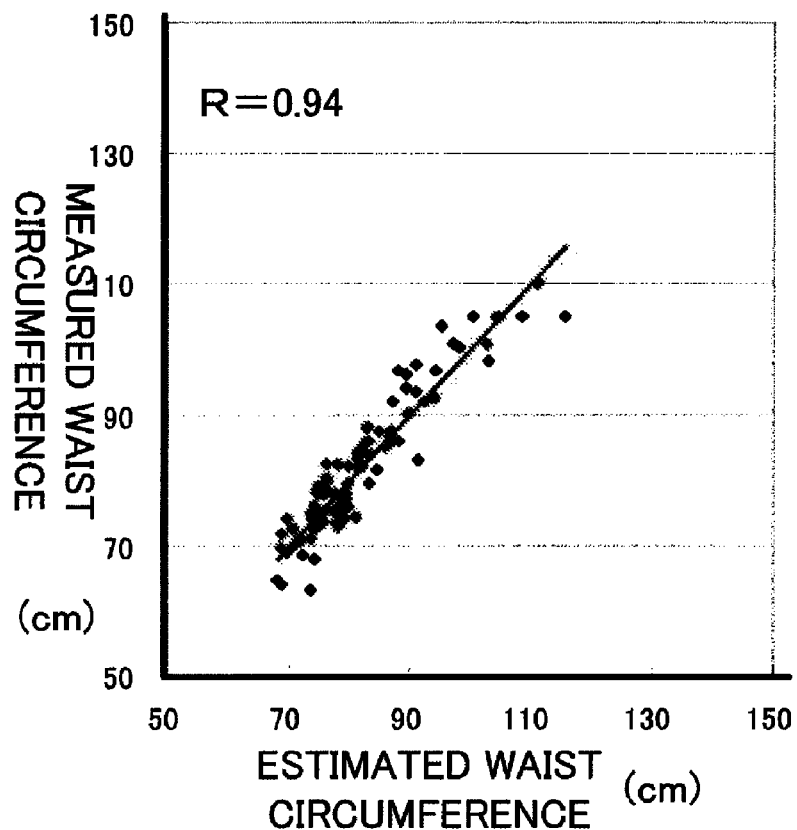
FIG. 18 is a graph showing a relationship between actually measured waist circumference and estimated waist circumference in accordance with Equation (12)

In the waist circumference computing process (Step S12), CPU 170 may estimate waist circumference WC in accordance with Equation (12) as follows:

$$WC=w4+w9*FAT+w2*W \qquad (12)$$

where w2, w4, and w9 are constants, W is weight, FAT is body fat mass. Body fat mass FAT is computed by multiplying weight W and body fat percentage % Fat estimated in Step S10. Equation (12) differs from Equation (6) in that Equation (12) has the second term having body fat mass FAT as a parameter. Like the above first mode, the constants w2, w4, and w9 may be preferably changed depending on sex. By selecting proper values of the constants w2, w4, and w9 for male human subjects, a correlation index R of "0.94" is obtained as shown in FIG. 18. Thus, using body fat mass FAT as a parameter enhances the accuracy in the estimation.

(8) Eighth Mode

Figure 19:
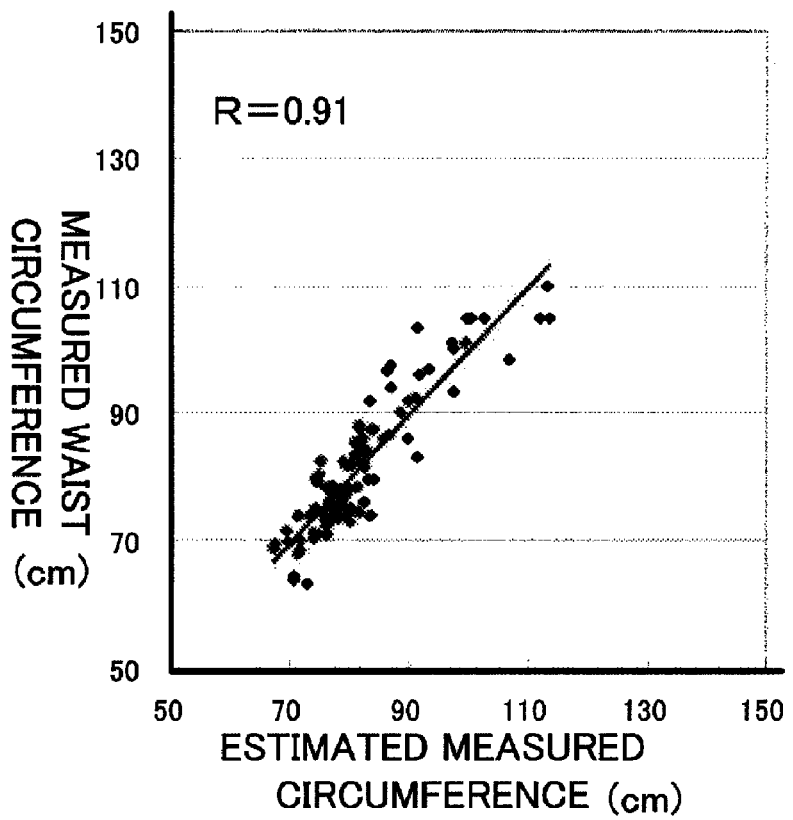
FIG. 19 is a graph showing a relationship between actually measured waist circumference and estimated waist circumference in accordance with Equation (13)

In the waist circumference computing process (Step S12), CPU 170 may estimate waist circumference WC in accordance with Equation (13) as follows:

$$WC = w4 + w10*FAT/H + w2*W \quad (13)$$

where w2, w4, and w10 are constants, W is weight, FAT is body fat mass, and H is height. Body fat mass FAT is computed by multiplying weight W and body fat percentage % Fat estimated in Step S10. Equation (13) differs from Equation (6) in that Equation (13) has the second term that has a parameter obtained by dividing body fat mass FAT by height H. Like the above first mode, the constants w2, w4, and w10 may be preferably changed depending on sex. By selecting proper values of the constants w2, w4, and w10 for male human subjects, a correlation index R of "0.91" is obtained as shown in FIG. 19. Thus, using a parameter obtained by dividing body fat mass FAT by the height H enhances the accuracy of the estimation.

(9) Ninth Mode

In the waist circumference computing process (Step S12), CPU 170 may estimate waist circumference WC in accordance with Equation (14) as follows:

$$WC = w4 + w11*\%Fat + w2*W \quad (14)$$

where w2, w4, and w11 are constants, W is weight, % Fat is body fat percentage, and H is height.

Figure 20:
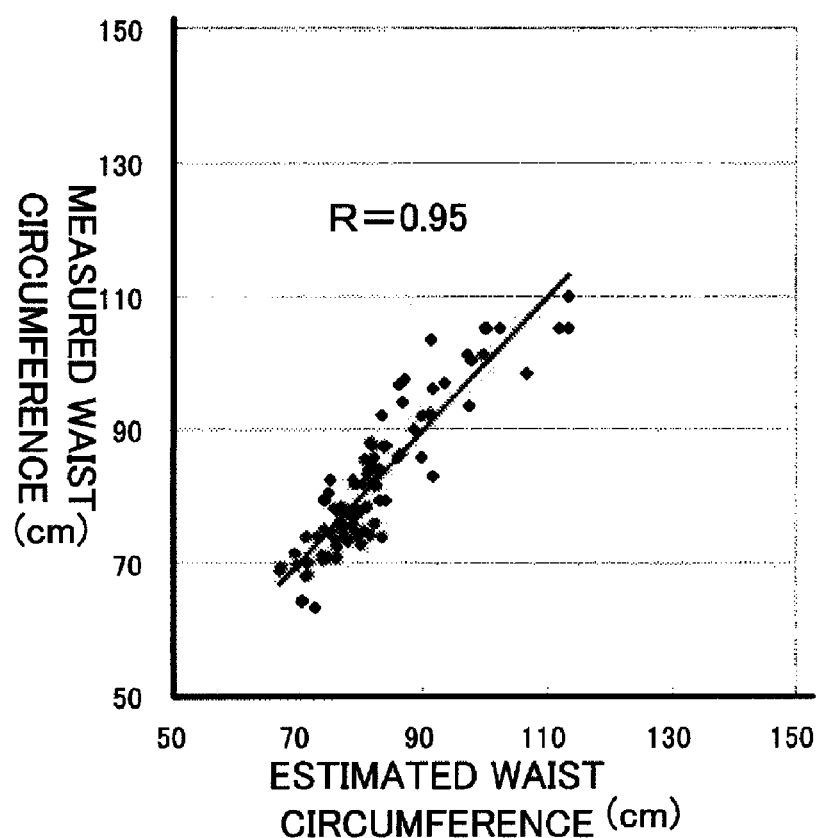
FIG. 20 is a graph showing a relationship between actually measured waist circumference and estimated waist circumference in accordance with Equation (14)

Equation (14) differs from Equation (6) in that Equation (14) has the second term that has body fat percentage % Fat as a parameter. Like the above first mode, the constants w2, w4, and w11 may be preferably changed depending on sex. By selecting proper values of the constants w2, w4, and w11 for male human subjects, a correlation index R of "0.95" is obtained as shown in FIG. 20. Thus, using body fat percentage % Fat as a parameter enhances the accuracy in the estimation.

2. Second Embodiment

The human subject index estimation apparatus 1 as described in the first embodiment measures bioelectric impedance Z between the bottom of the left foot and that of the right foot, based on which estimation is performed of body fat percentage % Fat, visceral fat cross-sectional area VFA, body fat mass FAT, waist circumference WC, and hip circumference HC. The human subject index estimation apparatus 2 of the second embodiment differs from human subject index estimation apparatus 1 of the first embodiment shown in FIG. 1 in that the apparatus 2 is provided with electrodes for both hands, by the use of which the bioelectric impedance Z of the trunk is more accurately measured.

Figure 21:
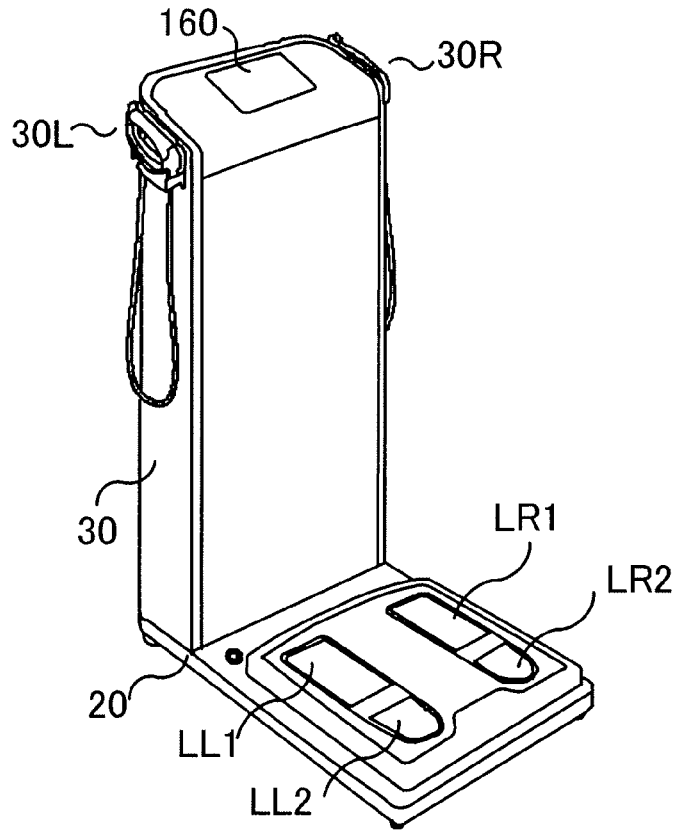
FIG. 21 is a perspective view showing an external configuration of a human subject index estimation apparatus according to a second embodiment.

FIG. 21 shows an external schematic view of human subject index estimation apparatus 2 of the second embodiment. Human subject index estimation apparatus 2 is L-shaped and is provided with a pillar-shaped box 30 on top of a base 20. Provided on base 20 are electrodes LL1 and LL2 for the left foot and electrodes LR1 and LR2 for the right foot. Furthermore, display unit 160 is provided in the top portion of box 30. Display unit 160 is a touch panel and also functions as an input unit through which information such as height, age, and sex is input. Provided on the left and right side surfaces of box 30 are an electrode unit 30L for the left hand and an electrode unit 30R for the right hand.

Figure 22:
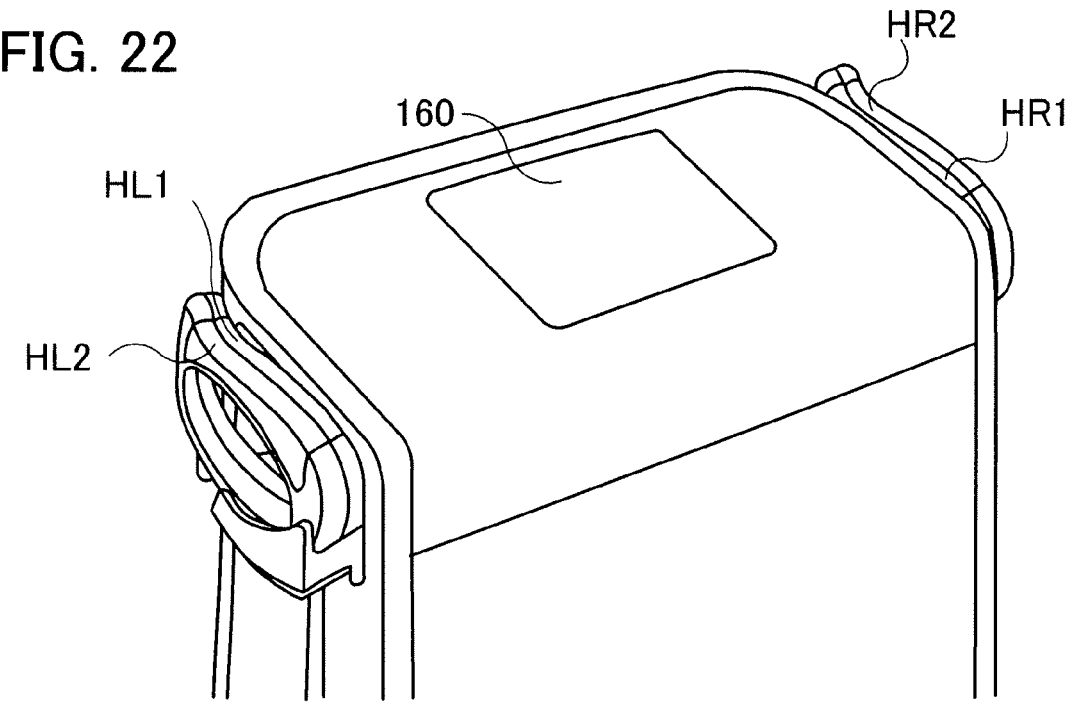
FIG. 22 is an enlarged view of a portion of the apparatus.

FIG. 22 is an enlarged view of the top portion of body 30. As shown in the figure, electrode unit 30L for the left hand has electrodes HL1 and HL2, and electrode unit 30R for the right hand has electrodes HR1 and HR2. Electrodes HL1 and HR1 function as those for supplying the standard current $I_{ref}$ (current source electrodes), and the electrode HL2 and HR2 function as those for detecting the potential difference (detection electrodes).

Figure 23:
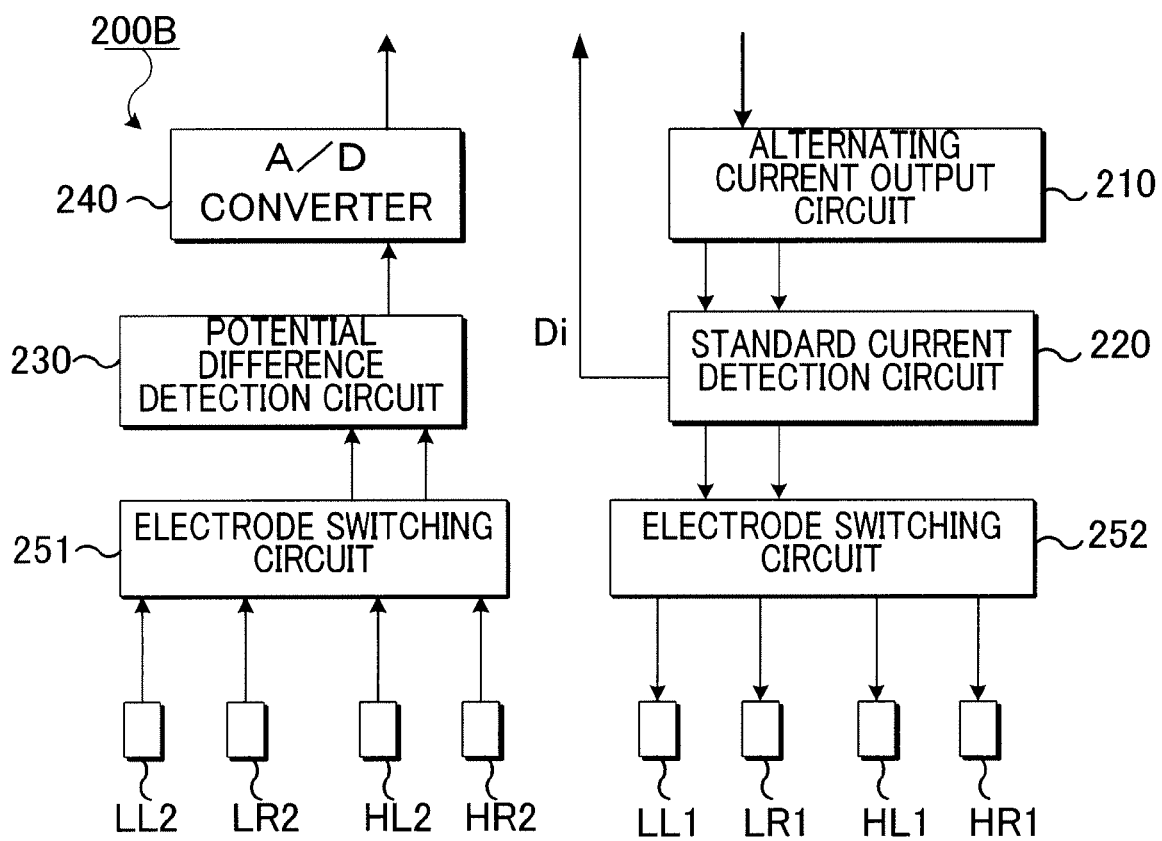
FIG. 23 is a block diagram showing a configuration of a bioelectric impedance measurement unit used in the apparatus.

Human subject index estimation apparatus 2 has a bioelectric impedance measurement unit 200B instead of having bioelectric impedance measurement unit 200A of the first embodiment. FIG. 23 shows a configuration of bioelectric impedance measurement unit 200B. Bioelectric impedance measurement unit 200B has the same configuration as bioelectric impedance measurement unit 200A as shown in FIG. 1 except that bioelectric impedance measurement unit 200B has electrode switching circuits 251 and 252, and electrodes HL1, HL2, HR1, and HR2. Electrode switching circuits 251 and 252 select electrodes to be used for the measurement of bioelectric impedance Z under control of CPU 170.

Figure 24A:
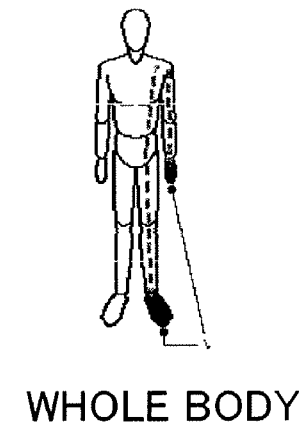
FIGS. 24A to 24E are diagrams for describing measurement of bioelectric impedance.
Figure 24A:
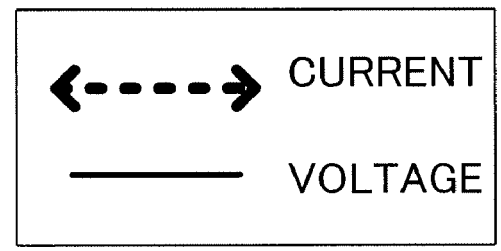
Figure 24B:
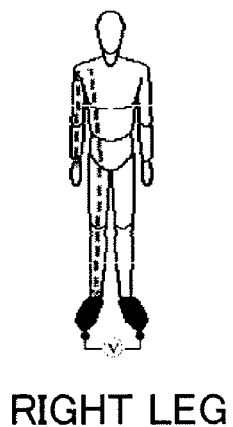
Figure 24B:
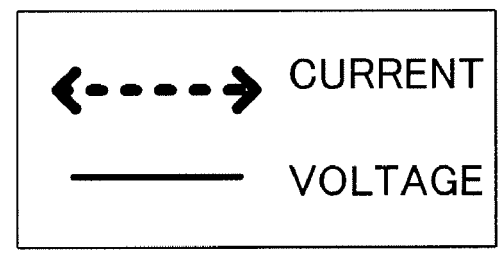

Bioelectric impedance measurement unit 200B has eight electrodes to be mounted on the hands and on the feet. The bioelectric impedance Z of a certain portion of a human body can be measured by properly selecting a subset of four electrodes from among these eight electrodes. For example, as shown in FIG. 24A, the bioelectric impedance Z of the whole body can be measured by supplying the standard current $I_{ref}$ to the electrode LL1 for the left foot and the electrode HL1 for the left hand and measuring a potential difference between the electrode LL2 for the left foot and the electrode HL2 for the left hand. As shown in FIG. 24B, the bioelectric impedance Z of the right leg can be measured by supplying the standard current $I_{ref}$ to the electrode LR1 for the right foot and the electrode HR1 for the right hand and measuring a potential difference between the electrode LR2 for the right foot and the electrode LL2 for the left foot.

Figure 24C:
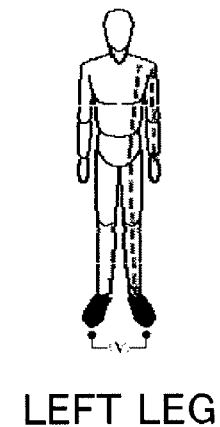
Figure 24C:
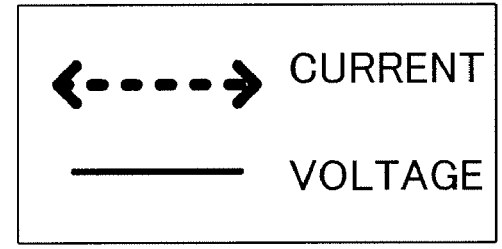
Figure 24D:
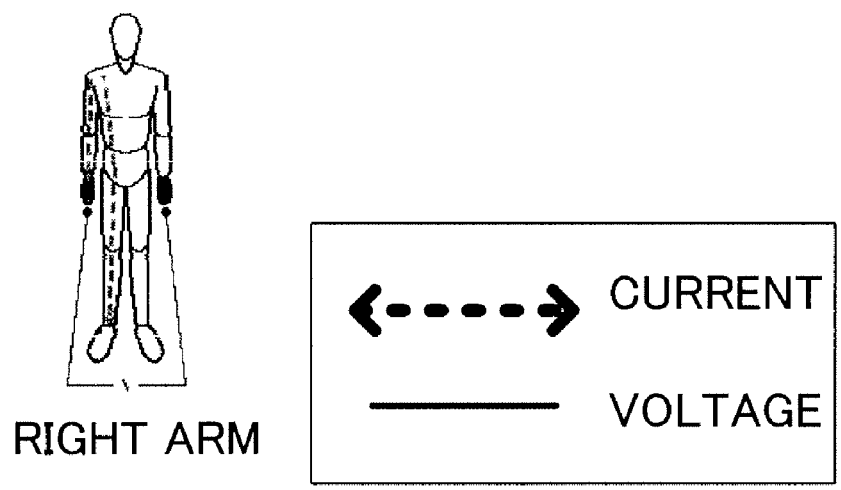
Figure 24E:
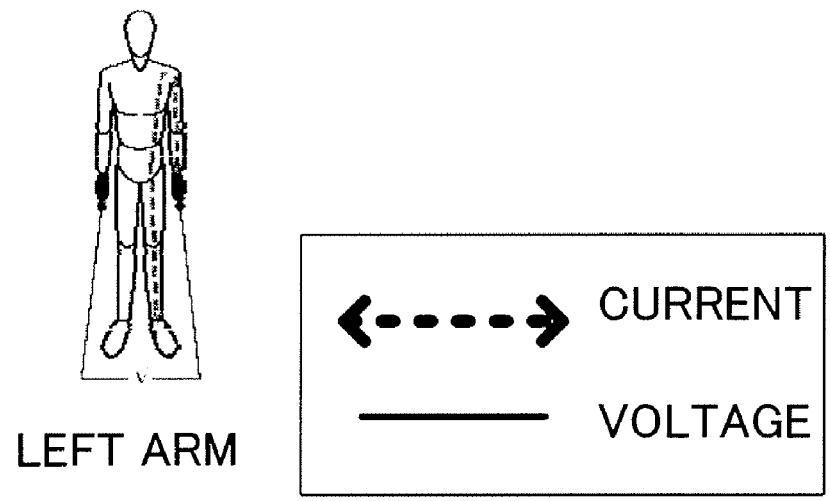

As shown in FIG. 24C, the bioelectric impedance Z of the left leg can be measured by supplying the standard current $I_{ref}$ to the electrode LL1 for the left foot and the electrode HL1 for the left hand and measuring a potential difference between the electrode LL2 for the left foot and the electrode LR2 for the right foot. As shown in FIG. 24D, the bioelectric impedance Z of the right arm can be measured by supplying the standard current $I_{ref}$ to the electrode HR1 for the right hand and the electrode LR1 for the right foot and measuring a potential difference between the electrode HR2 for the right hand and the electrode HL2 for the left hand. Furthermore, as shown in FIG. 24E, the bioelectric impedance Z of the left arm can be measured by supplying the standard current $I_{ref}$ to the electrode HL1 for the left hand and the electrode LL1 for the left foot and measuring a potential difference between the electrode HR2 for the right hand and the electrode HL2 for the left hand.

In the first embodiment, bioelectric impedance Z is measured between the bottom of the left foot and bottom of the right foot. The measured bioelectric impedance Z is used to estimate waist circumference WC and hip circumference HC. That is, bioelectric impedance Z is used as a parameter for expressing body fat mass in a predetermined portion such as the levels of the waist or the hips. However, since bioelectric impedance Z is measured between the bottom of the left foot and the bottom of the right foot, the measured impedance includes that of the legs, which is only slightly related to the body fat mass of the waist or the hips. Therefore, if the bioelectric impedance is measured at the trunk that is highly related to the waist and hips, the accuracy can be increased in estimating the waist circumference WC or the hip circumference HC.

The bioelectric impedance Z of the trunk can be obtained by measuring the bioelectric impedance of multiple portions of a human body and performing a computation based on the measured results. For example, the bioelectric impedance Z of the trunk can be obtained by subtracting the bioelectric impedance of the left arm and that of the left leg from that of the whole body. That is, given that the bioelectric impedance of the whole body is Zwb, that of the left leg is ZLL, and that of the left arm is ZLH, the bioelectric impedance of the trunk portion is derived from the following Equation (15):

$$Zx = Zwb - ZLL - ZLH \quad (15)$$

In the bioelectric impedance measurement process of Step S8 of the first embodiment, CPU 170 of the human subject index estimation apparatus 2, instead of measuring foot-to-foot bioelectric impedance, measures the bioelectric impedance of the whole body Zwb, that of the left leg ZLL, and that of the left arm ZLH, and obtains the bioelectric impedance of the trunk Zx in accordance with Equation (15).

In the body fat percentage computing process of Step S10 and in the visceral fat cross-sectional area, CPU 170 may compute, based on the bioelectric impedance of the trunk Zx, the body fat percentage % Fat and the visceral fat cross-sectional area VFA, respectively, instead of using the foot-to-foot bioelectric impedance Z.

Furthermore, CPU 170, in the waist circumference computing process of Step S12, 1) estimates body fat mass FATx of the trunk, and 2) computes waist circumference WC using the estimated body fat mass FATx.

CPU 170 first computes the body fat mass FATx of the trunk in accordance with the following Equation (16):

$$FATx = f3 * Zx * W/H^2 + f4 \quad (16)$$

where f3 and f4 are constants, W is weight, H is height, and $W/H^2$ is body mass index BMI.

Figure 25:
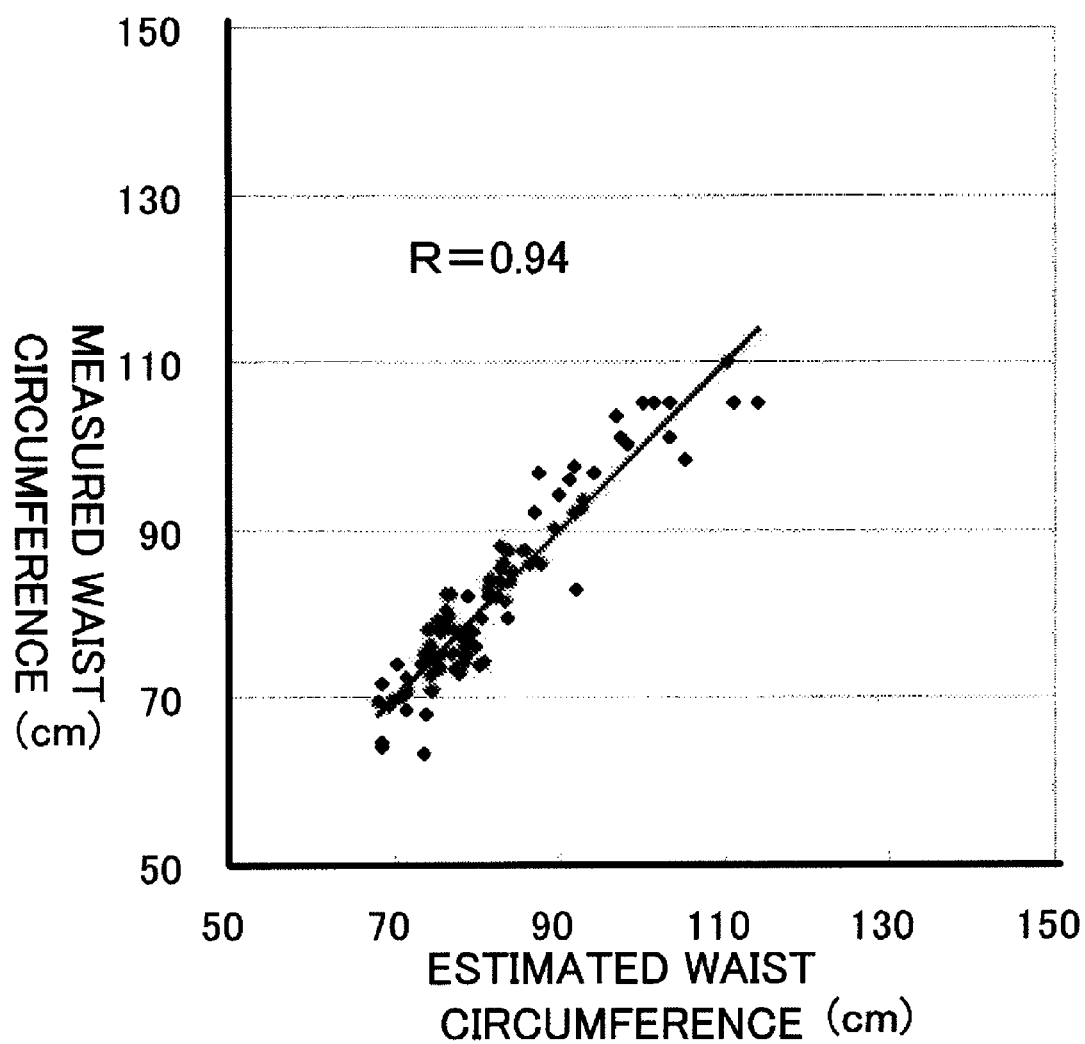
FIG. 25 is a graph showing a relationship between actually measured waist circumference and estimated waist circumference in accordance with Equation (17).

CPU 170 then computes the waist circumference WC using the estimated body fat mass FATx of the trunk in accordance with the following Equation (17):

$$WC = w4 + w2 * W + w12 * FATx \quad (17)$$

where w2, w4, and w12 are constants. In a case in which the constants w2, w4, and w12 are properly determined, the correlation index R is "0.94" as shown in FIG. 25. That is, using the body fat mass FATx as a parameter enhances the accuracy of the estimation.

It should be noted that the measuring method of the bioelectric impedance Zx of the trunk is not limited to the above-described method. That is, current source electrodes and detection electrodes can be selected as appropriate to measure bioelectric impedance Z of various portions of a human body such as an arm, leg, and the whole body. The bioelectric impedance Zx of the trunk portion may then be computed by adding or subtracting the results of various measurements.

3. Modifications

The present invention is not limited to the above embodiments, and various modifications, such as those described below, can be made.

(1) In each of the above embodiments, hip circumference HC and waist circumference WC are similar in that they are the circumference at the trunk of the body. Therefore, Equations (3), (6) to (14) and (17) for computing the waist circumference WC can be used to estimate the hip circumference HC by properly determining the values of the constants.

(2) In each of the above embodiments and modifications, waist circumference WC and hip circumference HC are estimated by performing a predetermined computation by using, as variables, sex, age, height, age, body fat percentage, and body fat mass, in addition to weight, each of the variables having a correlation with waist circumference WC and hip circumference HC. Therefore, waist circumference WC and hip circumference HC may be estimated using weight and at least one of sex, age, height, age, body fat percentage, and body fat mass. Furthermore, the circumference of a predetermined position between the levels of the abdomen and the buttocks is correlated with an amount of fat regardless of its position. Therefore, the circumference of a predetermined position between the levels of the abdomen and the buttocks may be estimated by using the above computations. Race or ethnic groups may also be used as a variable. Since the physiques of Asians and Europeans differ, waist circumference WC and hip circumference HC are more accurately estimated by using race as a variable. In particular, since the tendency in the physique can be identified by the pair of race and sex, it is preferable to change the constants depending on these variables.

In summary, CPU 170 may estimate circumference Y by computing Y=A1+A2*W+f(k), where Y is a circumference of a predetermined position, W is weight, A1 and A2 are constants, and f(k) is a function having, as a variable "k", at least one of sex, race, height, a body mass index, bioelectric impedance, body fat percentage, and body fat mass.

(3) In the above-described human subject index measuring apparatuses 1 and 2, the waist circumference WC and the hip circumference HC may be input using input unit in the first time measurement to compute the increased or decreased value of the waist circumference WC and the hip circumference HC based on measured indices such as weight W and bioelectric impedance Z. In the second and subsequent measurements, the waist circumference WC and the hip circumference HC may then be computed based on the computed increased or decreased value. Specifically, the waist circumference WCn and the hip circumference HCn in the second time and subsequent time measurements, with the "n" being a natural number that is equal to or larger than 2, may be computed by using the above-described Equations (3) and (5) as shown in the following Equations (18) and (19), respectively:

$$\begin{aligned} WCn &= WCini + \Delta WC \\ &= WCini + w1 * \{(Zn - Zini)/H\} + w2 * \\ &\quad (Wn - wini) + w3 * E \end{aligned} \quad (18)$$

$$\begin{aligned} HCn &= HCini + \Delta HC \\ &= HCini + h1 * (\%Fatn - \%Fatini) * \\ &\quad (Wn - Wini)/H^2 + h2 * (Wn - Wini) \end{aligned} \quad (19)$$

where ΔWC is an increased or decreased value of waist circumference WC and ΔHC is that of hip circumference HC, WCini is an initial value of waist circumference WC that is input by the operator, HCini is an initial value of hip circumference HC that is input by the operator, Zini is an initial value of bioelectric impedance Z, and %Fatini is an initial value of body fat percentage %Fat. CPU 170 stores the above initial values in third storage unit 140.

Furthermore, WCn is waist circumference WC for the n-time measurement, HCn is hip circumference HC for the n-time measurement, Wn is weight W for the n-time measurement, Zn is bioelectric impedance Z for the n-time measurement, and %Fatn is body fat percentage %Fat for the n-time measurement.

In Equations (18) and (19), actually measured values are used as initial values WCini and HCini so that increased or decreased values ΔWC and ΔHC are estimated.

Variables used in Equation (18) are Z, H, W, and E. "Zn-Zini" and "Wn-Wini" are variable difference values that are differences between variables Zn, Wn read from third storage unit 140 and initial values of variables Zini, Wini, respectively. It is assumed here that height and age remain unchanged.

CPU 170 computes a variable difference value for each variable. The computed variable difference values, instead of the measured variables, are used in performing the computation of Equation (3), thereby deriving an increased or decreased value ΔWC. Furthermore, CPU 170 totals an initial value of the circumference WCini read from third storage unit 140 and the derived increased or decreased value ΔWC to obtain the waist circumference WCn in this time measurement (i.e., n-time measurement).

Since the ratio of increased or decreased value ΔWC in the waist circumference WCn and the ratio of ΔHC in the hip circumference HCn are usually only a few percent, the ratio of estimation can be reduced. As a result, the accuracy can be increased in measuring the waist circumference WC and the hip circumference HC.

(4) In each of the above embodiments and modifications, the input unit is used to input basic information of a human subject such as height, age, and sex, but the present invention is not limited thereto. The basic information may be supplied to human subject index estimation apparatus 1 or 2 in the form of digital data. For example, the input unit may be provided with a communication device so that information can be supplied from a portable phone and a USB memory device.

What is claimed is:

1. A human subject index estimation apparatus that estimates a circumference of a human subject at a predetermined position between levels of the waist and the hips inclusive, comprising:
a weight scale that measures a weight of the human subject; and
a computer that executes a computation in accordance with an equation (A) thereby estimating the circumference, wherein the equation (A) is:

$$Y=a1*W+f(k) \quad (A)$$

wherein:
Y is the circumference,
W is the weight,
a1 is a constant,
k is a variable, and
f(k) is a function of at least one variable, the at least one variable including at least one of sex, race, age, height, body mass index, bioelectric impedance, body fat percentage, and body fat mass,
wherein the predetermined position is at the level of the waist, wherein the computer executes the computation of the equation (A) using, as the function f(k), a function f(Z, H,E) as shown in an equation (B) which is:

$$f(Z,H,E)=a2*Z/H+a3*E \quad (B)$$

wherein:
Z is bioelectric impedance,
H is height,
E is age, and
a2 and a3 are constants.

2. A human subject index estimation apparatus according to claim 1,
wherein the computer changes the constant a1 and a constant contained in the function f(k) depending on at least one of sex and race of the human subject.

3. A human subject index estimation apparatus according to claim 1,
wherein the predetermined position is at the level of the hips,
wherein the computer executes the computation of the equation (A) using, as the function f(k), a function f(% Fat,BMI) as shown in an equation (C) which is:

$$f(\% Fat,BMI)=a4*\% Fat*BMI \quad (C)$$

wherein:
%Fat is body fat percentage,
BMI is body mass index, and
a4 is a constant.

4. A human subject index estimation apparatus according to claim 1, further comprising a bioelectric impedance measurement device that measures bioelectric impedance between the left foot and the right foot,
wherein the computer executes the computation of the equation (A) using the measured bioelectric impedance.

5. A human subject index estimation apparatus that estimates a circumference of a human subject at a predetermined position between levels of the waist and the hips inclusive, comprising:
a weight scale that measures a weight of the human subject; and
a computer that executes a computation in accordance with an equation (A) thereby estimating the circumference, wherein the equation (A) is:

$$Y=a1*W+f(k) \quad (A)$$

wherein:
Y is the circumference,
W is the weight,
a1 is a constant,
k is a variable, and
f(k) is a function of plural variables, the plural variables including bioelectric impedance and at least one of sex, race, age, height, body mass index, body fat percentage, and body fat mass,
the human subject index estimation apparatus further comprising a bioelectric impedance measurement device that comprises:
first, second, third, and fourth electrodes contacting a left foot, a right foot, a left hand, and a right hand, respectively;
fifth, sixth, seventh, and eighth electrodes contacting a left foot, a right foot, a left hand, and a right hand, respectively;
an electric current supplier that supplies an electric current between two of the first, second, third, and fourth electrodes; and a potential difference detector that detects a potential difference between two of the fifth, sixth, seventh, and eighth electrodes;
wherein the bioelectric impedance measurement device switches the two electrodes to which the electric current is supplied and the two electrodes between which a potential difference is detected, to measure the bioelectric impedance of plural portions of the human subject, and the bioelectric impedance measurement device computes a bioelectric impedance of a trunk of the human subject based on the measured bioelectric impedance of the plural portions; and
wherein the computer executes the computation of the equation (A) using the measured bioelectric impedance.

6. A human subject index estimation apparatus according to claim 5,
wherein the computer changes the constant a1 and a constant contained in the function f(k) depending on at least one of sex and race of the human subject.

7. A human subject index estimation apparatus according to claim 5,
wherein the predetermined position is at the level of the waist,
wherein the computer executes the computation of the equation (A) using, as the function f(k), a function f(Z, H,E) as shown in an equation (B) which is:

$$f(Z,H,E)=a2*Z/H+a3*E \quad (B)$$

wherein:
Z is bioelectric impedance,
H is height,
E is age, and
a2 and a3 are constants.

8. A human subject index estimation apparatus according to claim 5,
wherein the predetermined position is at the level of the hips,
wherein the computer executes the computation of the equation (A) using, as the function f(k), a function f(%Fat,BMI) as shown in an equation (C) which is:

$$f(\% Fat,BMI)=a4*\% Fat*BMI \quad (C)$$

wherein:
% Fat is body fat percentage,
BMI is body mass index, and
a4 is a constant.

9. A human subject index estimation apparatus that estimates a circumference of a human subject at a predetermined position between levels of the waist and the hips inclusive, comprising:
a weight scale that measures a weight of the human subject; and
a computer that executes a computation in accordance with an equation (A) thereby estimating the circumference, wherein the equation (A) is:

$$Y=a1*W+f(k) \quad (A)$$

wherein:
Y is the circumference,
W is the weight,
a1 is a constant,
k is a variable, and
f(k) is a function of at least one variable, the at least one variable including at least one of sex, race, age, height, body mass index, bioelectric impedance, body fat percentage, and body fat mass, the human subject index estimation apparatus further comprising a storage unit that stores the circumference measured at the predetermined location as an initial circumference value and stores the variable measured in a measurement of a first time as an initial variable value,
wherein the computer, in a measurement at a second time and subsequent times, i) computes a variable difference value that is a difference between the variable measured at this time and the initial variable value read from the storage unit, ii) executes the computation of the equation (A) using the variable difference value instead of using the variable, thereby to compute one of an increased value and a decreased value of the circumference, and iii) computes the circumference as estimated at this time by adding the increased or decreased value of the circumference to the initial circumference value read from the storage unit.

10. A human subject index estimation apparatus according to claim 9,
wherein the computer changes the constant a1 and a constant contained in the function f(k) depending on at least one of sex and race of the human subject.

11. A human subject index estimation apparatus according to claim 9,
wherein the predetermined position is at the level of the waist,
wherein the computer executes the computation of the equation (A) using, as the function f(k), a function f(Z, H,E) as shown in an equation (B) which is:

$$f(Z,H,E)=a2*Z/H+a3*E \quad (B)$$

wherein:
Z is bioelectric impedance,
H is height,
E is age, and
a2 and a3 are constants.

12. A human subject index estimation apparatus according to claim 9,
wherein the predetermined position is at the level of the hips,
wherein the computer executes the computation of the equation (A) using, as the function f(k), a function f(%Fat,BMI) as shown in an equation (C) which is:

$$f(\% Fat,BMI)=a4*\% Fat*BMI \quad (C)$$

wherein:
% Fat is body fat percentage,
BMI is body mass index, and
a4 is a constant.

13. A human subject index estimation apparatus according to claim 9, further comprising a bioelectric impedance measurement device that measures bioelectric impedance between the left foot and the right foot,
wherein the computer executes the computation of the equation (A) using the measured bioelectric impedance.

14. A human subject index estimating method for estimating a circumference of a human subject at a predetermined position between levels of the waist and the hips inclusive, comprising:
measuring a body weight of the human subject; and
executing a computation in accordance with an equation (A) thereby estimating the circumference, wherein the equation (A) is:

$$Y=a1*W+f(k) \quad (A)$$

wherein:
Y is the circumference,

W is the weight,
a1 is a constant,
k is a variable, and
f(k) is a function of at least one variable, the at least one variable including at least one of sex, race, age, height, body mass index, bioelectric impedance, body fat percentage, and body fat mass,
wherein the predetermined position is at the level of the waist,
wherein the step of executing the computation in accordance with the equation (A) includes using, as the function f(k), a function f(Z,H,E) as shown in an equation (B) which is:

$$f(Z,H,E)=a2*Z/H+a3*E \tag{B}$$

wherein:
Z is bioelectric impedance,
H is height,
E is age, and
a2 and a3 are constants.

15. A human subject index estimating method for estimating a circumference of a human subject at a predetermined position between levels of the waist and the hips inclusive, comprising:
measuring a body weight of the human subject; and
executing a computation in accordance with an equation (A) thereby estimating the circumference, wherein the equation (A) is:

$$Y=a1*W+f(k) \tag{A}$$

wherein:
Y is the circumference,
W is the weight,
a1 is a constant,
k is a variable, and
f(k) is a function of plural variables, the variables including bioelectric impedance and at least one of sex, race, age, height, body mass index, body fat percentage, and body fat mass,
wherein the bioelectric impedance is measured by a bioelectric impedance measurement device that comprises: first, second, third, and fourth electrodes contacting a left foot, a right foot, a left hand, and a right hand, respectively; fifth, sixth, seventh, and eighth electrodes contacting a left foot, a right foot, a left hand, and a right hand, respectively; an electric current supplier that supplies an electric current between two of the first, second, third, and fourth electrodes; and a potential difference detector that detects a potential difference between two of the fifth, sixth, seventh, and eighth electrodes, and
wherein the bioelectric impedance measurement device switches the two electrodes to which the electric current is supplied and the two electrodes between which a potential difference is detected, to measure the bioelectric impedance of plural portions of the human subject, and the bioelectric impedance measurement device computes a bioelectric impedance of a trunk of the human subject based on the measured bioelectric impedance of the plural portions.

16. A human subject index estimating method for estimating a circumference of a human subject at a predetermined position between levels of the waist and the hips inclusive, comprising:
measuring a body weight of the human subject; and
executing a computation in accordance with an equation (A) thereby estimating the circumference, wherein the equation (A) is:

$$Y=a1*W+f(k) \tag{A}$$

wherein:
Y is the circumference,
W is the weight,
a1 is a constant,
k is a variable, and
f(k) is a function of at least one variable, the at least one variable including at least one of sex, race, age, height, body mass index, bioelectric impedance, body fat percentage, and body fat mass,
wherein the estimating of the circumference, in a measurement at a second time and subsequent times, includes:
i) storing, in a storage unit, the circumference measured at the predetermined location as an initial circumference value and the variable measured in a measurement of a first time as the initial variable value;
ii) computing a variable difference value that is a difference between the variable measured at this time and the initial variable value read from the storage unit;
iii) executing the computation of the equation (A) using the variable difference value instead of using the variable, thereby to compute one of an increased value and a decreased value of the circumference; and
iv) computing the circumference as estimated at this time by adding the increased or decreased value of the circumference to the initial circumference value read from the storage unit.

* * * * *